(12) United States Patent
Yanagawa et al.

(10) Patent No.: US 9,382,173 B2
(45) Date of Patent: Jul. 5, 2016

(54) METHOD OF PRODUCING SINGLE-RING AROMATIC HYDROCARBONS

(75) Inventors: Shinichiro Yanagawa, Tokyo (JP); Ryoji Ida, Tokyo (JP); Yasuyuki Iwasa, Tokyo (JP); Masahide Kobayashi, Tokyo (JP); Susumu Yasui, Yokohama (JP); Yoshishige Sugi, Yokohama (JP); Atsushi Fukui, Kawasaki (JP); Atsuro Nagumo, Kawasaki (JP)

(73) Assignees: JX Nippon Oil & Energy Corporation, Tokyo (JP); CHIYODA CORPORATION, Yokohama-shi, Kanagawa (JP)

( * ) Notice: Subject to any disclaimer, the term of this patent is extended or adjusted under 35 U.S.C. 154(b) by 229 days.

(21) Appl. No.: 14/006,974

(22) PCT Filed: Mar. 23, 2012

(86) PCT No.: PCT/JP2012/057432
§ 371 (c)(1),
(2), (4) Date: Nov. 15, 2013

(87) PCT Pub. No.: WO2012/133138
PCT Pub. Date: Oct. 4, 2012

(65) Prior Publication Data
US 2014/0066672 A1 Mar. 6, 2014

(30) Foreign Application Priority Data
Mar. 25, 2011 (JP) ................. P2011-067690
Mar. 25, 2011 (JP) ................. P2011-067691

(51) Int. Cl.
C07C 2/42 (2006.01)
C07C 2/76 (2006.01)
(Continued)

(52) U.S. Cl.
CPC ... *C07C 5/10* (2013.01); *C07C 4/06* (2013.01); *C10G 11/05* (2013.01); *C10G 35/095* (2013.01);
(Continued)

(58) Field of Classification Search
CPC .............. C07C 2/42; C07C 2/76; C07C 5/11; C07C 57/00
USPC ......... 585/319, 418, 266, 268; 208/62, 67, 49
See application file for complete search history.

(56) References Cited

U.S. PATENT DOCUMENTS
3,755,141 A 8/1973 Youngblood et al.
3,806,443 A 4/1974 Maziuk
(Continued)

FOREIGN PATENT DOCUMENTS
CN 101028985 A 9/2007
CN 101376823 A 3/2009
(Continued)

OTHER PUBLICATIONS
Extended European Search Report issued Aug. 4, 2014 in EP Application No. 12764115.7.
(Continued)

*Primary Examiner* — Thuan D Dang
(74) *Attorney, Agent, or Firm* — Panitch Schwarze Belisario & Nadel LLP

(57) ABSTRACT

Provided is a method for producing monocyclic aromatic hydrocarbons having 6 to 8 carbon atoms, the method including a cracking reforming reaction step of bringing feedstock oil into contact with a catalyst to effect a reaction; a step of purifying and recovering monocyclic aromatic hydrocarbons separated from the reaction step; and (1) a step of hydrogenating a heavy fraction separated from the reaction step; a dilution step of returning a portion of the hydrogenation product as a diluent oil to the hydrogenation step; and a step of returning the hydrogenation product to the reaction step; or (2) a step of adding a diluent to the heavy fraction separated from the reaction step; a step of hydrogenating the mixture; and a step of returning the hydrogenation product to the reaction step.

16 Claims, 4 Drawing Sheets

(51) Int. Cl.
  *C07C 5/11* (2006.01)
  *C07C 57/00* (2006.01)
  *C07C 5/10* (2006.01)
  *C10G 69/04* (2006.01)
  *C10G 11/05* (2006.01)
  *C10G 35/095* (2006.01)
  *C10G 61/02* (2006.01)
  *C07C 4/06* (2006.01)

(52) U.S. Cl.
  CPC ............... *C10G 61/02* (2013.01); *C10G 69/04* (2013.01); *C10G 2300/4081* (2013.01); *C10G 2300/802* (2013.01); *C10G 2400/30* (2013.01); *Y02P 20/132* (2015.11)

(56) References Cited

U.S. PATENT DOCUMENTS

| | | | |
|---|---|---|---|
| 4,053,388 A | 10/1977 | Bailey | |
| 5,582,711 A | 12/1996 | Ellis et al. | |
| 8,912,377 B2* | 12/2014 | Kim | C10G 11/02 585/256 |
| 2004/0215042 A1* | 10/2004 | Bottcher | C07C 5/10 585/400 |
| 2005/0077211 A1 | 4/2005 | Catani et al. | |

FOREIGN PATENT DOCUMENTS

| | | |
|---|---|---|
| JP | S49-41323 A | 4/1974 |
| JP | S53-116328 A | 10/1978 |
| JP | H03-002128 A | 1/1991 |
| JP | H03-026791 A | 2/1991 |
| JP | H03-052993 A | 3/1991 |
| JP | 2008-545035 A | 12/2008 |
| JP | 2009-235247 A | 10/2009 |
| JP | 2009-235248 A | 10/2009 |
| JP | 2012-062255 A | 3/2012 |
| WO | 9859019 A1 | 12/1998 |
| WO | 2007003709 A1 | 1/2007 |
| WO | 2009041508 A1 | 4/2009 |
| WO | 2010044562 A2 | 4/2010 |
| WO | 2010109899 A1 | 9/2010 |
| WO | 2011118753 A1 | 9/2011 |

OTHER PUBLICATIONS

Office Action issued Aug. 4, 2014 in CN Application No. 201280020101.4.

Office Action issued Oct. 7, 2014 in JP Application No. 2011-067691.

Int'l Search Report issued Jun. 5, 2012 in Int'l Application No. PCT/JP2012/057432.

* cited by examiner

METHOD OF PRODUCING SINGLE-RING AROMATIC HYDROCARBONS

CROSS-REFERENCE TO RELATED APPLICATION

This application is a Section 371 of International Application No. PCT/JP2012/057432, filed Mar. 23, 2012, which was published in the Japanese language on Oct. 4, 2012, under International Publication No. WO 2012/133138 A1, and the disclosure of which is incorporated herein by reference.

TECHNICAL FIELD

The present invention relates to a method for producing a monocyclic aromatic hydrocarbon.

Priority is claimed on Japanese Patent Application No. 2011-067690 and Japanese Patent Application No. 2011-067691, filed Mar. 25, 2011, the contents of which are incorporated herein by reference.

BACKGROUND ART

Light cycle oil (hereinafter, referred to as "LCO"), which is cracked light oil produced with a fluid catalytic cracking (hereinafter, referred to as "FCC") units, contains a large amount of polycyclic aromatic hydrocarbons, and have been utilized as diesel or fuel oil. However, in recent years, investigations have been conducted to obtain monocyclic aromatic hydrocarbons having 6 to 8 carbon atoms with a high added value (for example, benzene, toluene, xylene, and ethylbenzene) that can be utilized as high octane gasoline base materials or petroleum chemistry feedstocks, from the LCO.

For example, in PTL 1 to PTL 3, there have been suggested methods for producing a monocyclic aromatic hydrocarbon from a polycyclic aromatic hydrocarbon that is contained in LCO or the like in a large amount, using a zeolite catalyst.

CITATION LIST

Patent Literature

[PTL 1] Japanese Unexamined Patent Application, First Publication No. H3-2128
[PTL 2] Japanese Unexamined Patent Application, First Publication No. H3-52993
[PTL 3] Japanese Unexamined Patent Application, First Publication No. H3-26791

SUMMARY OF INVENTION

Technical Problem

However, in the methods described in Patent Documents 1 to 3, it cannot be said that the yield of monocyclic aromatic hydrocarbons having 6 to 8 carbon atoms is sufficiently high.

Thus, it is contemplated that in order to sufficiently increase the yield of monocyclic aromatic hydrocarbons, the LCO or the like is subjected to cracking reforming, the product thus obtained is hydrogenated, and these hydrogenation products are recycled again to a cracking reforming reaction step.

Here, the product obtainable by subjecting LCO or the like to cracking reforming contains a large amount (for example, 50 mass % to 95 mass %) of polycyclic aromatic hydrocarbons in the heavy fraction. Polycyclic aromatic hydrocarbons may vary depending on the composition of the feedstock oil, but mainly include bicyclic aromatic hydrocarbons. Therefore, the polycyclic aromatic hydrocarbons serve as a satisfactory feedstock for monocyclic aromatic hydrocarbons through partial hydrogenation. Therefore, as described above, the yield of the monocyclic aromatic hydrocarbons can be sufficiently increased by recycling hydrogenation products of polycyclic aromatic hydrocarbons and supplying the hydrogenation product again to a cracking reforming reaction step.

However, the hydrogenation of bicyclic aromatic (polycyclic aromatic) hydrocarbons is an exothermic reaction, and the amount of heat generation is very large. Therefore, when the product containing such polycyclic aromatic hydrocarbons in a large amount is hydrogenated, the reaction temperature at the reactor extremely increases, and it is difficult to carry out an appropriate reaction in conventional facilities. Furthermore, for example, it is possible to suppress an increase in the reaction temperature and achieve an appropriate reaction by supplying hydrogen stepwise from the middle of the reactor (hydrogen quench or the like); however, in that case, the apparatus configuration of the reactor is complicated, and a sharp increase in the facility cost is brought about.

The present invention was achieved in view of such circumstances, and an object of the invention is to provide a method for producing monocyclic aromatic hydrocarbons, which can produce monocyclic aromatic hydrocarbons having 6 to 8 carbon atoms with a high yield from a feedstock oil containing polycyclic aromatic hydrocarbons, and can suppress extreme heat generation at the time of the hydrogenation so that a sharp increase in the facility cost of the hydrogenation reactor can be avoided.

Solution to Problem

The present invention relates to a method for producing monocyclic aromatic hydrocarbons, by which monocyclic aromatic hydrocarbons having 6 to 8 carbon atoms are produced from a feedstock oil having a 10 vol % distillation temperature of 140° C. or higher and a 90 vol % distillation temperature of 380° C. or lower, the method including:

a cracking reforming reaction step of bringing the feedstock oil into contact with a catalyst for monocyclic aromatic hydrocarbon production containing a crystalline aluminosilicate to effect a reaction, thereby obtaining a product containing monocyclic aromatic hydrocarbons having 6 to 8 carbon atoms and a heavy fraction having 9 or more carbon atoms;

a hydrogenation step of hydrogenating a liquid fraction separated from the product produced in the cracking reforming reaction step;

a dilution step of adding a portion of a hydrogenation product of the heavy fraction having 9 or more carbon atoms obtained in the hydrogenation step, or a diluent to the liquid fraction; and a recycling step of returning the other portion of the hydrogenation product of the heavy fraction obtained in the hydrogenation step to the cracking reforming reaction step.

More specifically, the method for producing monocyclic aromatic hydrocarbons related to a first aspect of the invention is a method for producing monocyclic aromatic hydrocarbons, by which monocyclic aromatic hydrocarbons having 6 to 8 carbon atoms are produced from a feedstock oil having a 10 vol % distillation temperature of 140° C. or higher and a 90 vol % distillation temperature of 380° C. or lower, the method including:

a cracking reforming reaction step of bringing the feedstock oil into contact with a catalyst for monocyclic aromatic hydrocarbon production containing a crystalline aluminosilicate to effect a react, thereby obtaining a product containing monocyclic aromatic hydrocarbons having 6 to 8 carbon atoms and a heavy fraction having 9 or more carbon atoms;

a purification/recovery step of purifying and recovering monocyclic aromatic hydrocarbons having 6 to 8 carbon atoms separated from the product produced in the cracking reforming reaction step;

a hydrogenation step of hydrogenating the heavy fraction having 9 or more carbon atoms separated from the product produced in the cracking reforming reaction step;

a dilution step of returning a portion of a hydrogenation product of the heavy fraction having 9 or more carbon atoms obtained in the hydrogenation step, as a diluent oil to the hydrogenation step; and a recycling step of returning the other portion of the hydrogenation product of the heavy fraction obtained in the hydrogenation step to the cracking reforming reaction step.

Furthermore, in regard to the method for producing monocyclic aromatic hydrocarbons, it is preferable that in the dilution step, the amount of the diluent oil that is returned to the hydrogenation step be adjusted such that the mass ratio of the heavy fraction having 9 or more carbon atoms separated from the product produced in the cracking reforming reaction step and supplied to the hydrogenation step, to the diluent oil is in the range of 10:90 to 80:20.

Furthermore, another method for producing monocyclic aromatic hydrocarbons of the invention is a method for producing monocyclic aromatic hydrocarbons, by which monocyclic aromatic hydrocarbons having 6 to 8 carbon atoms are produced from a feedstock oil having a 10 vol % distillation temperature of 140° C. or higher and a 90 vol % distillation temperature of 380° C. or lower, the method including:

a cracking reforming reaction step of bringing the feedstock oil into contact with a catalyst for monocyclic aromatic hydrocarbon production containing a crystalline aluminosilicate to effect a reaction, thereby obtaining a product containing monocyclic aromatic hydrocarbons having 6 to 8 carbon atoms and a heavy fraction having 9 or more carbon atoms;

a hydrogenation step of hydrogenating a portion separated from the product produced in the cracking reforming reaction step;

a purification/recovery step of distilling the hydrogenation product obtained in the hydrogenation step to purify monocyclic aromatic hydrocarbons having 6 to 8 carbon atoms, recovering the monocyclic aromatic hydrocarbons, and separating a heavy fraction having 9 or more carbon atoms from the monocyclic aromatic hydrocarbons having 6 to 8 carbon atoms;

a dilution step of returning a portion of the heavy fraction having 9 or more carbon atoms separated in the purification/recovery step, as a diluent oil to the hydrogenation step; and a recycling step of returning the other portion of the heavy fraction separated in the purification/recovery step to the cracking reforming reaction step.

Furthermore, in regard to the method for producing monocyclic aromatic hydrocarbons, it is preferable that in the dilution step, the amount of the diluent oil that is returned to the hydrogenation step be adjusted such that the mass ratio of the product separated from the product produced in the cracking reforming reaction step and supplied to the hydrogenation step, to the diluent oil is in the range of 20:80 to 80:20.

Furthermore, in regard to the method for producing monocyclic aromatic hydrocarbons, it is preferable that in the dilution step, the diluent oil be returned to the hydrogenation step such that the concentration of polycyclic aromatic hydrocarbons in a mixed oil of the product separated from the product produced in the cracking reforming reaction step and supplied to the hydrogenation step, and the diluent oil is 5 mass % to 50 mass %.

Furthermore, in regard to the method for producing monocyclic aromatic hydrocarbons, it is preferable that in the hydrogenation step, the hydrogenation pressure be set to 0.7 MPa to 13 MPa.

A method for producing monocyclic aromatic hydrocarbons related to a second aspect of the invention is a method for producing monocyclic aromatic hydrocarbons, by which monocyclic aromatic hydrocarbons having 6 to 8 carbon atoms are produced from a feedstock oil having a 10 vol % distillation temperature of 140° C. or higher and a 90 vol % distillation temperature of 380° C. or lower, the method including:

a cracking reforming reaction step of bringing the feedstock oil into contact with a catalyst for monocyclic aromatic hydrocarbon production containing a crystalline aluminosilicate to effect a reaction, thereby obtaining a product containing monocyclic aromatic hydrocarbons having 6 to 8 carbon atoms and a heavy fraction having 9 or more carbon atoms;

a purification/recovery step of purifying and recovering monocyclic aromatic hydrocarbons having 6 to 8 carbon atoms separated from the product produced in the cracking reforming reaction step;

a dilution step of adding a diluent comprising hydrocarbons to the heavy fraction having 9 or more carbon atoms separated from the product produced in the cracking reforming reaction step;

a hydrogenation step of hydrogenating the mixture; and a recycling step of returning the hydrogenation product of the mixture obtained in the hydrogenation step to the cracking reforming reaction step.

Furthermore, in regard to the method for producing monocyclic aromatic hydrocarbons, it is preferable that the method include a diluent recovering step of separating and removing the diluent from the hydrogenation product of the mixture obtained in the hydrogenation step, recovering the diluent, and reutilizing the diluent as a diluent to be added to the heavy fraction having 9 or more carbon atoms.

Furthermore, in regard to the method for producing monocyclic aromatic hydrocarbons, it is preferable to use a hydrocarbon oil having a boiling point of lower than 185° C. as the diluent.

Furthermore, in regard to the method for producing monocyclic aromatic hydrocarbons, it is preferable to use a substance having a concentration of polycyclic aromatic hydrocarbons of 50 mass % or less as the diluent.

Furthermore, in regard to the method for producing monocyclic aromatic hydrocarbons, it is preferable that in the dilution step, the amount of the diluent be adjusted such that the mass ratio of the heavy fraction having 9 or more carbon atoms separated from the product produced in the cracking reforming reaction step and supplied to the hydrogenation step, to the diluent is in the range of 10:90 to 80:20.

Furthermore, in regard to the method for producing monocyclic aromatic hydrocarbons, it is preferable that in the dilution step, a diluent be added such that the concentration of polycyclic aromatic hydrocarbons in a mixture obtainable by adding a diluent to the heavy fraction having 9 or more carbon atoms is 5 mass % to 50 mass %.

Furthermore, in regard to the method for producing monocyclic aromatic hydrocarbons, it is preferable that in the hydrogenation step, the hydrogenation pressure be set to 0.7 MPa to 13 MPa.

Advantageous Effects of Invention

According to the method for producing monocyclic aromatic hydrocarbons of the invention, monocyclic aromatic hydrocarbons having 6 to 8 carbon atoms can be produced from a feedstock oil containing polycyclic aromatic hydrocarbons with a high yield. Furthermore, since the method includes a dilution step, extreme heat generation attributable to the hydrogenation of polycyclic aromatic hydrocarbons in the hydrogenation step is suppressed, and thereby a stabilized hydrogenation is enabled. Thus, a sharp increase in the facility cost of the hydrogenation reactor can be avoided.

DESCRIPTION OF EMBODIMENTS

First Aspect

Exemplary Embodiment 1

Hereinafter, Exemplary Embodiment 1 of the method for producing monocyclic aromatic hydrocarbons related to the first aspect of the invention will be described.

Figure 1:
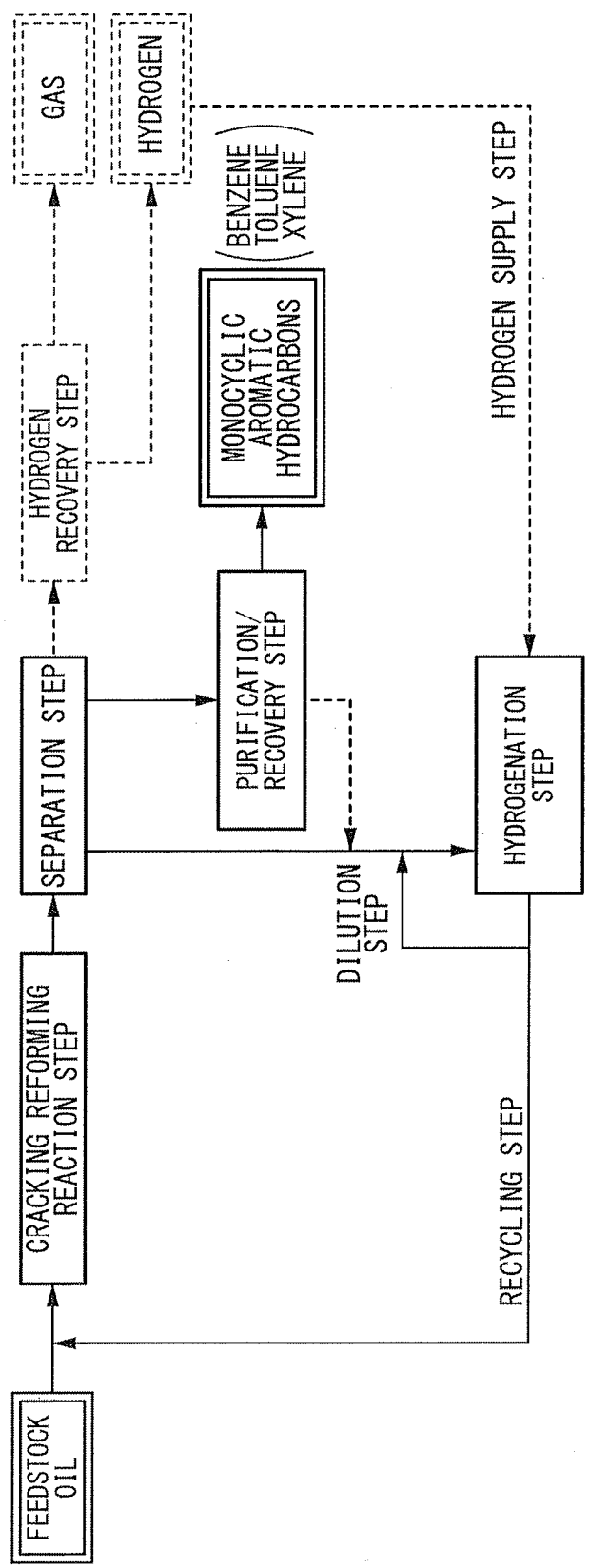
FIG. 1 is a diagram for illustrating Exemplary Embodiment 1 of the method for producing monocyclic aromatic hydrocarbons related to a first aspect of the invention.

FIG. 1 is a diagram for illustrating Exemplary Embodiment 1 of the method for producing monocyclic aromatic hydrocarbons related to the first aspect of the invention, and the method for producing monocyclic aromatic hydrocarbons of the present exemplary embodiment is a method of producing monocyclic aromatic hydrocarbons having 6 to 8 carbon atoms from the feedstock oil.

That is, the method for producing monocyclic aromatic hydrocarbons of the present exemplary embodiment is, as illustrated in FIG. 1:

(a-1) a cracking reforming reaction step of bringing a feedstock oil into contact with a catalyst for monocyclic aromatic hydrocarbon production to effect a reaction, thereby obtaining a product containing monocyclic aromatic hydrocarbons having 6 to 8 carbon atoms and a heavy fraction having 9 or more carbon atoms;

(b-1) a separation step of separating the product produced in the cracking reforming reaction step into plural fractions;

(c-1) a purification/recovery step of purifying and recovering monocyclic aromatic hydrocarbons separated in the separation step;

(d-1) a hydrogenation step of hydrogenating whole or a portion of the heavy fraction having 9 or more carbon atoms obtainable from the fractions separated in the separation step;

(e-1) a dilution step of returning a portion of the hydrogenation product of the heavy fraction having 9 or more carbon atoms obtained in the hydrogenation step to the hydrogenation step;

(f-1) a recycling step of returning the residual portion of the hydrogenation product of the heavy fraction obtained in the hydrogenation step to the cracking reforming reaction step;

(g-1) a hydrogen recovery step of recovering hydrogen produced as a by-product in the cracking reforming reaction step from the gas components separated in the separation step; and (h-1) a hydrogenation supply step of supplying the hydrogen collected in the hydrogen recovery step to the hydrogenation step.

Among the steps (a-1) to (h-1), the steps (a-1), (c-1) (d-1), (e-1), and (f-1) are essential steps for Exemplary Embodiment 1 of the first aspect of the invention, and the steps (b-1), (g-1), and (h-1) are optional steps.

Hereinafter, the respective steps will be described in detail.

<Cracking Reforming Reaction Step>

In the cracking reforming reaction step, a feedstock oil is brought into contact with a catalyst for monocyclic aromatic hydrocarbon production, and using saturated hydrocarbons contained in the feedstock oil as a hydrogen donating source, polycyclic aromatic hydrocarbons are partially hydrogenated by a hydrogen transfer reaction from the saturated hydrocarbons. Thus, ring-opening is carried out, and thereby the polycyclic aromatic hydrocarbons are converted to monocyclic aromatic hydrocarbons. Furthermore, the saturated hydrocarbons that are present in the feedstock oil or are obtainable in a separation operation can also be converted to monocyclic aromatic hydrocarbons through cyclization and dehydrogenation. Also, monocyclic aromatic hydrocarbons having 6 to 8 carbon atoms can also be obtained by cracking monocyclic aromatic hydrocarbons having 9 or more carbon atoms. Thereby, a product containing monocyclic aromatic hydrocarbons having 6 to 8 carbon atoms and a heavy fraction having 9 or more carbon atoms is obtained.

This product includes, in addition to the monocyclic aromatic hydrocarbons or the heavy fraction, hydrogen, methane, ethane, ethylene, LPG (propane, propylene, butane, butene and the like), and the like. Furthermore, the heavy fraction includes a large amount of bicyclic aromatic hydrocarbons such as naphthalene, methylnaphthalene and dimethylnaphthalene, and also, aromatic hydrocarbons having three or more rings, such as anthracene, may also be included depending on the feedstock oil. In the present application, these bicyclic aromatic hydrocarbons and aromatic hydrocarbons having three or more rings are collectively described as polycyclic aromatic hydrocarbons.

In this cracking reforming reaction step, regarding components such as naphthenobenzenes, paraffins and naphthenes in the feedstock oil, a majority of the components are lost by producing monocyclic aromatic hydrocarbons. Furthermore, polycyclic aromatic hydrocarbons are such that a portion thereof is converted to monocyclic aromatic hydrocarbons by cracking and hydrogen transfer with saturated hydrocarbons, but at the same time, as alkyl side chains are cleaved, bicyclic aromatic hydrocarbons having fewer side chains, such as naphthalene, methylnaphthalene and dimethylnaphthalene, are also mainly produced as by-products. Therefore, in this cracking reforming reaction step, monocyclic aromatic hydrocarbons are produced with a high yield, and at the same time, bicyclic aromatic hydrocarbons are also produced as by-products as a heavy fraction having 9 or more carbon atoms.

(Feedstock Oil)

The feedstock oil used in the invention is an oil having a 10 vol % distillation temperature of 140° C. or higher and a 90 vol % distillation temperature of 380° C. or lower. Regarding an oil having a 10 vol % distillation temperature of lower than 140° C., since the oil is light oil, monocyclic aromatic hydrocarbons are produced, so that the oil does not suit the purpose of the invention. Furthermore, in the case of using an oil having a 90 vol % distillation temperature of higher than 380° C., the yield of monocyclic aromatic hydrocarbons is decreased, the amount of coke deposition on the catalyst for monocyclic aromatic hydrocarbon production increases, and a rapid decrease in the catalyst activity tends to occur.

The 10 vol % distillation temperature of the feedstock oil is preferably 150° C. or higher, and the 90 vol % distillation temperature of the feedstock oil is preferably 360° C. or lower.

In addition, the 10 vol % distillation temperature and the 90 vol % distillation temperature as used herein mean values measured according to JIS K2254 "Petroleum products—Distillation Testing Methods."

Examples of feedstock oils having a 10 vol % distillation temperature of 140° C. or higher and a 90 vol % distillation temperature of 380° C. or lower include LCO, hydrogenation purified oil of LCO, coal liquefaction oil, heavy oil hydrocracking purified oil, straight run kerosene, straight run gas oil, coker kerosene, coker gas oil, and oil sand hydrocracking purified oil.

Polycyclic aromatic hydrocarbons are materials that have low reactivity and are not easily converted to monocyclic aromatic hydrocarbons in the cracking reforming reaction step of the invention. However, on the other hand, when hydrogenated in the hydrogenation step, polycyclic aromatic hydrocarbons are converted to naphthenobenzenes, and can be further converted to monocyclic aromatic hydrocarbons by being supplied to be recycled again to the cracking reforming reaction step. Therefore, the feedstock oil is not particularly limited in view of containing a large amount of polycyclic aromatic hydrocarbons. However, among the polycyclic aromatic hydrocarbons, aromatic hydrocarbons having three or more rings consume a large amount of hydrogen in the hydrogenation step, and even though those hydrocarbons are hydrogenation products, since the reactivity in the cracking reforming reaction step is low, it is not preferable for the feedstock oil to contain a large amount of the polycyclic aromatic hydrocarbons. Therefore, the content of aromatic hydrocarbons having three or more rings in the feedstock oil is preferably 25 vol % or less, and more preferably 15 vol % or less.

In addition, regarding the feedstock oil containing bicyclic aromatic hydrocarbons that are converted to naphthenobenzene in the hydrogenation step and intended to reduce aromatic hydrocarbons having three or more rings, for example, it is more preferable that the 90 vol % distillation temperature of the feedstock oil be 330° C. or lower.

Furthermore, the polycyclic aromatic hydrocarbons as used herein mean the total value of the content of bicyclic aromatic hydrocarbons (bicyclic aromatic fraction) and the content of aromatic hydrocarbons having three or more rings (tricyclic or higher-cyclic aromatic fraction) that are measured according to JPI-5S-49 "Petroleum products—Hydrocarbon type test methods—High performance liquid chromatography method", or analyzed by an FID gas chromatographic method or a two-dimensional gas chromatographic method. Hereinafter, when the contents of polycyclic aromatic hydrocarbons, bicyclic aromatic hydrocarbons, and aromatic hydrocarbons having three or more rings are expressed in vol %, the contents are values measured according to JPI-5S-49, and when the contents are expressed in mass %, the values are measured based on an FID gas chromatographic method or a two-dimensional gas chromatographic method.

(Reaction Type)

Regarding the reaction type at the time of bringing the feedstock oil into contact with a catalyst for monocyclic aromatic hydrocarbon production and causing the feedstock oil to react, examples thereof include a fixed bed, a moving bed, and a fluidized bed. In this invention, since a heavy fraction is used as the feedstock, a fluidized bed in which the coke fraction adhered to the catalyst can be continuously removed and the reaction can be carried out in a stable manner, is preferred, and a continuous regeneration type fluidized bed in which a catalyst is circulated between a reactor and a regenerator and thus reaction and regeneration can be continuously repeated, is particularly preferred. The feedstock oil at the time of bringing the catalyst for monocyclic aromatic hydrocarbon production into contact is preferably in a gaseous state. Furthermore, the feedstock may be diluted by means of a gas as necessary.

(Catalyst for Monocyclic Aromatic Hydrocarbon Production)

The catalyst for monocyclic aromatic hydrocarbon production contains a crystalline aluminosilicate.

[Crystalline Aluminosilicate]

The crystalline aluminosilicate is preferably a medium-pore zeolite and/or a large-pore zeolite, from the viewpoint that the yield of monocyclic aromatic hydrocarbons can be further increased.

A medium-pore zeolite is a zeolite having a 10-membered ring skeletal structure, and examples of the medium-pore zeolite include zeolites having crystal structures of AEL type, EUO type, FER type, HEU type, MEL type, MFI type, NES type, TON type, and WEI type. Among these, from the viewpoint of further increasing the yield of monocyclic aromatic hydrocarbons, MFI type is preferred.

A large-pore zeolite is a zeolite having a 12-membered ring skeletal structure, and examples of the large-pore zeolite include zeolites having crystal structures of AFI type, ATO type, BEA type, CON type, FAU type, GME type, LTL type, MOR type, MTW type, and OFF type. Among these, from the viewpoint of being industrially usable, zeolites of BEA type, FAU type and MOR type are preferred, and from the viewpoint of further increasing the yield of monocyclic aromatic hydrocarbons, a zeolite of BEA type is preferred.

The crystalline aluminosilicate may contain a small-pore zeolite having a 10-membered or fewer-membered ring skeletal structure, or an ultralarge-pore zeolite having a 14-membered or more-membered ring skeletal structure, in addition to the medium-pore zeolite and the large-pore zeolite.

Here, examples of the small-pore zeolite include zeolites having crystal structures of ANA type, CHA type, ERI type, GIS type, KFI type, LTA type, NAT type, PAU type, and YUG type.

Examples of the ultralarge-pore zeolite include zeolites having crystal structures of CLO type and VPI type.

When the cracking reforming reaction step is carried out by a fixed bed reaction, the content of the crystalline aluminosilicate in the catalyst for monocyclic aromatic hydrocarbon production is preferably 60 mass % to 100 mass %, more preferably 70 mass % to 100 mass %, and particularly preferably 90 mass % to 100 mass %, when the total amount of the catalyst for monocyclic aromatic hydrocarbon production is designated as 100 mass %. If the content of the crystalline aluminosilicate is 60 mass % or more, the yield of monocyclic aromatic hydrocarbons can be sufficiently increased.

When the cracking reforming reaction step is carried out by a fluidized bed reaction, the content of the crystalline aluminosilicate in the catalyst for monocyclic aromatic hydrocarbon production is preferably 20 mass % to 60 mass %, more preferably 30 mass % to 60 mass %, and particularly preferably 35 mass % to 60 mass %, when the total amount of the catalyst for monocyclic aromatic hydrocarbon production is designated as 100 mass %. If the content of the crystalline aluminosilicate is 20 mass % or more, the yield of monocyclic aromatic hydrocarbons can be sufficiently increased. If the content of the crystalline aluminosilicate is more than 60 mass %, the content of the binder that can be incorporated into the catalyst is reduced, and the catalyst may become unsuitable for fluidized bed applications.

[Gallium and Zinc]

The catalyst for monocyclic aromatic hydrocarbon production can contain gallium and/or zinc as necessary. When gallium and/or zinc is incorporated, the production proportion of the monocyclic aromatic hydrocarbons can be further increased.

Examples of the form of gallium incorporation in the catalyst for monocyclic aromatic hydrocarbon production include a form in which gallium is incorporated into the lattice skeleton of the crystalline aluminosilicate (crystalline aluminogallosilicate), a form in which gallium is supported on the crystalline aluminosilicate (gallium-supported crystalline aluminosilicate), and a form including both.

Examples of the form of zinc incorporation in the catalyst for monocyclic aromatic hydrocarbon production include a form in which zinc is incorporated into the lattice skeleton of the crystalline aluminosilicate (crystalline aluminozincosilicate), a form in which zinc is supported in the crystalline aluminosilicate (zinc-supported crystalline aluminosilicate), and a form including both.

A crystalline aluminogallosilicate and a crystalline aluminozincosilicate have a structure in which $SiO_4$, $AlO_4$ and $GaO_4/ZnO_4$ structures exist in the skeleton. Furthermore, the crystalline aluminogallosilicate and crystalline aluminozincosilicate are obtained by, for example, gel crystallization based on hydrothermal synthesis, a method of inserting gallium or zinc into the lattice skeleton of a crystalline aluminosilicate, or a method of inserting aluminum into the lattice skeleton of a crystalline gallosilicate or a crystalline zincosilicate.

A gallium-supported crystalline aluminosilicate is a material in which gallium is supported on a crystalline aluminosilicate according to a known method such as an ion exchange method or an impregnation method. The gallium source used at that time is not particularly limited, but examples thereof include gallium salts such as gallium nitrate and gallium chloride, and gallium oxide.

A zinc-supported crystalline aluminosilicate is a material in which zinc is supported on a crystalline aluminosilicate according to a known method such as an ion exchange method or an impregnation method. The zinc source used at that time is not particularly limited, but examples thereof include zinc salts such as zinc nitrate and zinc chloride, and zinc oxide.

When the catalyst for monocyclic aromatic hydrocarbon production contains gallium and/or zinc, the content of gallium and/or zinc in the catalyst for monocyclic aromatic hydrocarbon production is preferably 0.01 mass % to 5.0 mass %, and more preferably 0.05 mass % to 2.0 mass %, when the total amount of the catalyst is designated as 100 mass %. If the content of gallium and/or zinc is 0.01 mass % or more, the production proportion of the monocyclic aromatic hydrocarbons can be further increased, and if the content is 5.0 mass % or less, the yield of the monocyclic aromatic hydrocarbons can be further increased.

[Phosphorus and Boron]

For the catalyst for monocyclic aromatic hydrocarbon production, it is preferable that the catalyst contain phosphorus and/or boron. When the catalyst for monocyclic aromatic hydrocarbon production contains phosphorus and/or boron, a decrease over time in the yield of the monocyclic aromatic hydrocarbons can be prevented, and coke production at the catalyst surface can be suppressed.

Examples of the method for incorporating phosphorus into the catalyst for monocyclic aromatic hydrocarbon production include a method of supporting phosphorus on a crystalline aluminosilicate, a crystalline aluminogallosilicate, or a crystalline aluminozincosilicate by means of an ion exchange method, an impregnation method or the like; a method of incorporating a phosphorus compound at the time of zeolite synthesis, and thereby substituting a portion in the skeleton of a crystalline aluminosilicate with phosphorus; and a method of using a crystallization accelerator containing phosphorus at the time of zeolite synthesis. The phosphate ion-containing aqueous solution to be used at that time is not particularly limited, but aqueous solutions prepared by dissolving phosphoric acid, diammonium hydrogen phosphate, ammonium dihydrogen phosphate, and other water-soluble phosphoric acid salts in water at arbitrary concentrations can be preferably used.

Examples of the method for incorporating boron into the catalyst for monocyclic aromatic hydrocarbon production include a method of supporting boron on a crystalline aluminosilicate, a crystalline aluminogallosilicate, or a crystalline aluminozincosilicate by means of an ion exchange method, an impregnation method or the like; a method of incorporating a boron compound at the time of zeolite synthesis and thereby substituting a portion in the skeleton of a crystalline aluminosilicate with boron; and a method of using a crystallization accelerator containing boron at the time of zeolite synthesis.

The content of phosphorus and/or boron in the catalyst for monocyclic aromatic hydrocarbon production is preferably 0.1 mass % to 10 mass %, more preferably 0.5 mass % to 9 mass %, and even more preferably 0.5 mass % to 8 mass %, when the total amount of the catalyst is designated as 100 mass %. If the content of phosphorus and/or boron is 0.1 mass % or more, a decrease over time in the yield can be further prevented, and if the content is 10 mass % or less, the yield of the monocyclic aromatic hydrocarbons can be further increased.

[Shape]

The catalyst for monocyclic aromatic hydrocarbon production is formed into, for example, a powder form, a particulate form, or a pellet form, depending on the reaction type. For example, in the case of a fluidized bed, the catalyst is formed in a powder form, and in the case of a fixed bed, the catalyst is formed into a particulate form or a pellet form. The average particle size of the catalyst used in a fluidized bed is preferably 30 μm to 180 μm, and more preferably 50 μm to 100 μm. Furthermore, the bulk density of the catalyst used in a fluidized bed is preferably 0.4 g/cc to 1.8 g/cc, and more preferably 0.5 g/cc to 1.0 g/cc.

In addition, the average particle size represents a particle size which corresponds to 50 mass % in a particle size distribution obtained by classification with sieves, and the bulk density is a value measured by the method of JIS Standard R9301-2-3.

In the case of obtaining a particulate or pellet-shaped catalyst, according to necessity, an inert oxide is incorporated into the catalyst as a binder, and then the blend may be molded using various molding machines.

When the catalyst for monocyclic aromatic hydrocarbon production contains an inorganic oxide such as a binder, a binder containing phosphorus may be used without any problem.

(Reaction Temperature)

The reaction temperature at the time of bringing feedstock oil into contact with a catalyst for monocyclic aromatic hydrocarbon production to react, is not particularly limited, but the reaction temperature is preferably set to 400° C. to 650° C. If the lower limit of the reaction temperature is 400° C. or higher, the feedstock oil can be made to react easily, and the lower limit is more preferably 450° C. or higher. Furthermore, if the upper limit of the reaction temperature is 650° C. or lower, the yield of the monocyclic aromatic hydrocarbons can be sufficiently increased, and the upper limit is more preferably 600° C. or lower.

(Reaction Pressure)

The reaction pressure at the time of bringing feedstock oil into contact with a catalyst for monocyclic aromatic hydrocarbon production to react, is preferably set to 1.5 MPaG or less, and more preferably set to 1.0 MPaG or less. If the reaction pressure is 1.5 MPaG or less, production of by-products of light gas can be suppressed, and also, pressure resistance of the reaction apparatus can be lowered.

(Contact time)

In regard to the contact time for the feedstock oil and the catalyst for monocyclic aromatic hydrocarbon production, there are no particular limitations as long as a desired reaction substantially proceeds; however, for example, the contact time as the time for gas passage on the catalyst for monocyclic aromatic hydrocarbon production is preferably 1 second to 300 seconds, and it is more preferable to set the lower limit to 5 seconds and the upper limit to 150 seconds. If the contact time is 1 second or longer, the reaction can be carried out reliably, and if the contact time is 300 seconds or less, accumulation of carbonaceous materials on the catalyst due to coking or the like can be suppressed. Also, the amount of generation of light gas due to cracking can be suppressed.

<Separation Step>

In the separation step, the product produced in the cracking reforming reaction step is separated into plural fractions.

In order to separate the product into plural fractions, known distillation apparatuses and gas-liquid separation apparatuses may be used. An example of the distillation apparatuses may be an apparatus capable of separation by distillation into plural fractions by means of a multistage distillation apparatus such as a stripper. An example of the gas-liquid separation apparatus may be an apparatus including a gas-liquid separation tank; a product inlet pipe through which the product is introduced into the gas-liquid separation tank; a gas component outflow pipe that is provided in the upper part of the gas-liquid separation tank; and a liquid component outflow pipe that is provided in the lower part of the gas-liquid separation tank.

In the separation step, at least a gas component and a liquid fraction are separated, and also, the liquid fraction is further separated into plural fractions. Examples of such a separation step include a form of separating the product into a gas component mainly containing components having 4 or fewer carbon atoms (for example, hydrogen, methane, ethane, and LPG) and a liquid fraction; a form of separating the product into a gas component containing components having 2 or fewer carbon atoms (for example, hydrogen, methane, and ethane) and a liquid fraction; a form of further separating the liquid fraction into a fraction containing monocyclic aromatic hydrocarbons and a heavy fraction; a form of separating the liquid fraction again into LPG, a fraction containing monocyclic aromatic hydrocarbons, and a heavy fraction; and a form of separating the liquid fraction again into LPG, a fraction containing monocyclic aromatic hydrocarbons, and plural heavy fractions.

In this exemplary embodiment, a form of separating the product into a gas component containing components having 4 or fewer carbon atoms (for example, hydrogen, methane, ethane, and LPG) and a liquid fraction, and also, further separating the liquid fraction into a fraction containing monocyclic aromatic hydrocarbons having 6 to 8 carbon atoms and a fraction heavier than this (heavy fraction having 9 or more carbon atoms), is suitably employed. Here, the heavy fraction having 9 or more carbon atoms that is separated in the separation step may vary depending on the nature of the feedstock oil or the conditions for the cracking reforming reaction step, separation step and the like; however, the concentration of polycyclic aromatic hydrocarbons is as high as 50 mass % to 95 mass %.

<Purification/Recovery Step>

In the purification/recovery step, the monocyclic aromatic hydrocarbons having 6 to 8 carbon atoms obtained in the separation step is purified and collected.

In this purification/recovery step, since a fraction heavier than the monocyclic aromatic hydrocarbons is separated in the separation step, a step of recovering benzene/toluene/xylene from the fraction containing monocyclic aromatic hydrocarbons having 6 to 8 carbon atoms is employed. Here, the fraction heavier than monocyclic aromatic hydrocarbons is a heavy fraction having 9 or more carbon atoms, and contains polycyclic aromatic hydrocarbons as main components. Particularly, the heavy fraction contains a large amount of bicyclic aromatic hydrocarbons such as naphthalenes.

Further, when a form in which a liquid fraction is not fractionated is employed as the separation step, in this purification/recovery step, a step of separating and removing the fraction heavier than monocyclic aromatic hydrocarbons, and recovering monocyclic aromatic hydrocarbons or benzene/toluene/xylene (monocyclic aromatic hydrocarbons having 6 to 8 carbon atoms) is employed.

Furthermore, when the liquid fraction is not fractionated satisfactorily in the separation step, and when monocyclic aromatic hydrocarbons having 6 to 8 carbon atoms are collected, a fraction other than the monocyclic aromatic hydrocarbons is contained in a large amount, this fraction may be separated and supplied to, for example, the hydrogenation step that will be described below. The fraction heavier than the monocyclic aromatic hydrocarbons contains polycyclic aromatic hydrocarbons as main components, and particularly contains a large amount of bicyclic aromatic hydrocarbons such as naphthalenes.

<Hydrogenation Step>

In the hydrogenation step, all or a portion of the heavy fraction having 9 or more carbon atoms obtained from the fraction separated in the separation step is hydrogenated. Specifically, the heavy fraction and hydrogen are supplied to a hydrogenation reactor, and at least a portion of the polycyclic aromatic hydrocarbons contained in the heavy fraction is hydrogenation treated using a hydrogenation catalyst. Here, the heavy fraction that is separated in the separation step or the purification/recovery step and supplied to the hydrogenation step, that is, the heavy fraction having 9 or more carbon atoms, contains a large amount of bicyclic aromatic (polycyclic aromatic) hydrocarbons such as naphthalenes.

Thus, in the hydrogenation step, it is preferable to hydrogenate these polycyclic aromatic hydrocarbons until the hydrocarbons each have one aromatic ring. For example, naphthalene is preferably hydrogenated until it becomes tetraline (naphthenobenzene), and also, alkylnaphthalenes such as methylnaphthalene and dimethylnaphthalene are preferably converted to naphthenobenzene, that is, an aromatic hydrocarbon having one aromatic ring and having a tetraline skeleton. Similarly, indenes are preferably converted to aromatic hydrocarbons having an indane skeleton, anthracenes are preferably converted to aromatic hydrocarbons having an octahydroanthracene skeleton, and phenanthrenes are preferably converted to aromatic hydrocarbons having an octahydrophenanthrene skeleton.

Further, when a portion of the heavy fraction having 9 or more carbon atoms is not supplied to the hydrogenation step, the heavy fraction may also be used for the production of naphthalenes by separating naphthalene or the like, or may be used as a fuel base material.

If hydrogenation is carried out until the hydrocarbons have one aromatic ring each, when these hydrogenation products are returned to the cracking reforming reaction step at the recycling step that will be described below, the hydrogenation products, particularly aromatic hydrocarbons having a tetraline skeleton, are easily converted to monocyclic aromatic hydrocarbons. As such, in order to increase the yield of monocyclic aromatic hydrocarbons in the cracking reforming reaction step, the content of polycyclic aromatic hydrocarbons in the hydrogenation products obtainable in this hydrogenation step is preferably adjusted to 40 mass % or less, more preferably 25 mass % or less, and even more preferably 15 mass % or less.

Also, although the composition may vary depending on the operation conditions, under conventional conditions, the hydrogenation products obtainable in this hydrogenation step contains about several mass % to 30 mass % of bicyclic aromatic hydrocarbons, about 40 mass % to 90 mass % of monocyclic naphthenobenzene, and about several mass % to 30 mass % of bicyclic naphthene.

Furthermore, the content of polycyclic aromatic hydrocarbons in the hydrogenation products is preferably smaller than the content of polycyclic aromatic hydrocarbons in the feedstock oil. In regard to the content of polycyclic aromatic hydrocarbons in the hydrogenation products, that is, the concentration of polycyclic aromatic hydrocarbons, the concentration can be lowered by increasing the amount of the hydrogenation catalyst or by increasing the reaction pressure. However, it is not necessary to carry out the hydrogenation treatment until all of the polycyclic aromatic hydrocarbons become saturated hydrocarbons. Excessive hydrogenation brings about an increase in the amount of hydrogen consumption, and also causes an excessive increase in the amount of heat generation.

Regarding the reaction type in the hydrogenation step, a fixed bed is suitably employed.

Regarding the hydrogenation catalyst, known hydrogenation catalysts (for example, nickel catalysts, palladium catalysts, nickel-molybdenum-based catalysts, cobalt-molybdenum-based catalysts, nickel-cobalt-molybdenum-based catalysts, and nickel-tungsten-based catalysts) can be used.

The hydrogenation temperature may vary depending on the hydrogenation catalyst used, but the hydrogenation temperature is considered to be usually in the range of 100° C. to 450° C., more preferably 200° C. to 400° C., and even more preferably 250° C. to 380° C.

The hydrogenation pressure is preferably set to from 0.7 MPa to 13 MPa. Particularly, the hydrogenation pressure is more preferably set to from 1 MPa to 10 MPa, and even more preferably set to from 1 MPa to 7 MPa. If the hydrogenation pressure is set to 13 MPa or less, a hydrogenation reactor having a relatively low durable pressure can be used, and the facility cost can be reduced. Furthermore, since the pressure of hydrogen collected in the hydrogen recovery step is usually 13 MPa or less, the collected hydrogen can be used without increasing the pressure. On the other hand, if the hydrogenation pressure is set to 0.7 MPa or higher, the yield of the hydrogenation can be maintained sufficiently appropriately.

The amount of hydrogen consumption also varies depending on the amount of the diluent oil conveyed in the dilution step that will be described below, but the amount of hydrogen consumption is preferably 2000 scfb (337 $Nm^3/m^3$) or less, more preferably 1500 scfb (253 $Nm^3/m^3$) or less, and even more preferably 1000 scfb (169 $Nm^3/m^3$) or less.

On the other hand, the amount of hydrogen consumption is preferably 100 scfb (17 $Nm^3/m^3$) or more in view of the yield of the hydrogenation.

The liquid hourly space velocity (LHSV) is preferably set to from 0.1 $h^{-1}$ to 20 $h^{-1}$ and more preferably from 0.2 $h^{-1}$ to 10 $h^{-1}$. If the LHSV is set to 20 $h^{-1}$ or less, polycyclic aromatic hydrocarbons can be sufficiently hydrogenated at a lower hydrogenation pressure. On the other hand, when the LHSV is set to $0.1^{-1}$ or more, an increase in the scale of the hydrogenation reactor can be avoided.

Here, since polycyclic aromatic hydrocarbons, for example, bicyclic aromatic hydrocarbons occupying a majority thereof, have a large amount of heat generation at the time of the hydrogenation as described above, in the case of a feedstock having a high component ratio of polycyclic aromatic hydrocarbons, in order to carry out the reaction in a stable manner, it is preferable to employ a technique for suppressing an excessive increase in the reaction temperature. In this invention, regarding the method for suppressing the reaction temperature, a general technique can be employed, and techniques such as circulating hydrogen gas quenching that is employed in conventional kerosene-gas oil desulfurization apparatuses, and liquid quenching using a cooling oil, can be used. However, the heavy fraction that is separated in the separation step and is directly supplied to this hydrogenation step, has a very high concentration of polycyclic aromatic hydrocarbons, for example, as high as 50 mass % to 95 mass %, as described above. Therefore, if it is attempted to suppress heat generation only by circulating hydrogen gas quenching and/or liquid quenching, quenching facilities in a number close to a two-digit number are needed, and the configuration around the reaction apparatus for suppressing heat generation becomes very complicated. Furthermore, since the reaction apparatus becomes a reaction apparatus associated with an extremely large amount of heat generation, it is evaluated to be an apparatus with a high risk at the time of emergency.

Furthermore, it is difficult to control the hydrogenation itself, and the reaction in which bicyclic aromatic (polycyclic aromatic) hydrocarbons are converted to naphthenobenzene that is suitable as a feedstock for monocyclic aromatic hydrocarbons, is not carried out properly.

Thus, in the present exemplary embodiment, the concentration of polycyclic aromatic hydrocarbons in the heavy fraction that is supplied to the hydrogenation step is adjusted by the dilution step that will be described below, and heat generation occurring as a result of the hydrogenation of polycyclic aromatic hydrocarbons is suppressed. Thus, for example, a hydrogenation which is sufficiently adequate even with a conventional general hydrogenation reactor that is used for desulfurization of kerosene-gas oil, can be carried out. At the same time, by returning a portion of polycyclic aromatic hydrocarbons that have not reacted in the hydrogenation step again to the hydrogenation step, an effect of increasing the yield of monocyclic aromatic hydrocarbons is also obtained.

<Dilution Step>

In the dilution step, a portion of the hydrogenation product of the heavy fraction having 9 or more carbon atoms obtained in the hydrogenation step is returned as diluent oil to the hydrogenation step, and the concentration of the polycyclic aromatic hydrocarbons in the heavy fraction that is supplied to the hydrogenation step is decreased to an appropriate concentration. That is, the heavy fraction that is separated in the separation step and is directly supplied to the hydrogenation step (heavy fraction that is supplied separately from the diluent oil) has a very high concentration of polycyclic aromatic hydrocarbons, for example, as high as 50 mass % to 95 mass %, as described above. In this regard, in the hydrogenation step, since the polycyclic aromatic hydrocarbons in the heavy fraction supplied as described above are hydrogenated until the polycyclic aromatic hydrocarbons have one aromatic ring each, the concentration of polycyclic aromatic hydrocarbons in the hydrogenation product of the heavy fraction obtained in this hydrogenation step decreases to a large extent, for example, by about 5 mass % to 40 mass %, although the decrease may vary depending on the conditions for the hydrogenation.

Thus, as such, when a hydrogenation product with a decreased concentration of the polycyclic aromatic hydrocarbons is returned as diluent oil to the hydrogenation step, the concentration of polycyclic aromatic hydrocarbons in the heavy fraction having 9 or more carbon atoms that is supplied to the hydrogenation step can be decreased to an appropriate concentration.

Specifically, in this dilution step, it is preferable to return the diluent oil to the hydrogenation step such that the concentration of polycyclic aromatic hydrocarbons in a mixed oil composed of the product (heavy fraction having 9 or more carbon atoms) that is separated from the product produced in the cracking reforming reaction step and is supplied to the hydrogenation separately from the diluent oil and the diluents oil, that is, a mixed oil that is actually supplied to the hydrogenation step, is from 5 mass % to 50 mass %. Furthermore, it is more preferable to return the diluent oil such that the concentration of polycyclic aromatic hydrocarbons is from 15 mass % to 35 mass %.

When the concentration of the polycyclic aromatic hydrocarbons in the mixed oil is adjusted to 50 mass % or less, heat generation due to the hydrogenation is suppressed, so that an extreme increase in the reaction temperature at the hydrogenation reactor is prevented, and an appropriate hydrogenation (for example, conversion from bicyclic aromatic hydrocarbons to naphthenobenzenes) can be achieved. Furthermore, a general hydrogenation reactor can be used. Furthermore, by adjusting the concentration to 5 mass % or more, the conversion from polycyclic aromatic hydrocarbons to naphthenobenzenes, which is the main purpose of the hydrogenation step, can be achieved with desired efficiency.

However, if the concentration of polycyclic aromatic hydrocarbons in the mixed oil is too low, the conversion efficiency from the polycyclic aromatic hydrocarbons to naphthenobenzenes is lowered, so that the scale of the hydrogenation reactor is increased, which is not preferable. Therefore, in order to further increase the conversion efficiency, it is more preferable to adjust the concentration of polycyclic aromatic hydrocarbons to 15 mass % or more as described above. Furthermore, in order to suppress heat generation due to the hydrogenation more sufficiently, it is more preferable to adjust the concentration of polycyclic aromatic hydrocarbons to 35 mass % or less.

In this dilution step, in order to adjust the concentration of polycyclic aromatic hydrocarbons to a concentration such as described above, the amount of the diluent oil to be conveyed is appropriately determined. At that time, the amount of the diluent oil is largely affected by the concentration of the polycyclic aromatic hydrocarbons in the product (heavy fraction having 9 or more carbon atoms) that is separated from the product produced in the cracking reforming reaction step and is supplied to the hydrogenation step. That is, if the concentration of polycyclic aromatic hydrocarbons in the product is high, it is necessary to make the amount of the diluent oil relatively high, and if the concentration of polycyclic aromatic hydrocarbons in the product is low, the amount of the diluent oil can be relatively decreased.

Usually, the concentration of polycyclic aromatic hydrocarbons in the heavy fraction (product) that is directly supplied from the separation step to the hydrogenation step as described above is 50 mass % to 95 mass %.

Therefore, the concentration of polycyclic aromatic hydrocarbons in the heavy fraction (product) and the concentration of polycyclic aromatic hydrocarbons in the diluent oil are measured according to, for example, JPI-5S-49 "Petroleum products—Hydrocarbon type test methods—High performance liquid chromatographic method", or is identified by an FID gas chromatographic method, a two-dimensional gas chromatographic method or the like, and the mixing amounts of the heavy fraction (product) and the diluent oil are determined such that the concentration of polycyclic aromatic hydrocarbons in the mixed oil after being diluted with the diluent oil is 5 mass % to 50 mass %, and preferably 15 mass % to 35 mass %. Usually, the mass ratio (mixing ratio) of the heavy fraction that is directly supplied from the separation step to the hydrogenation step (heavy fraction having 9 or more carbon atoms that is separated from the product produced in the cracking reforming reaction step and is supplied to the hydrogenation step) and the diluent oil may vary depending on the concentration of polycyclic aromatic hydrocarbons in the heavy fraction (product) or the hydrogenation pressure at which the diluent oil is supplied; however, the mass ratio is adjusted to be in the range of 10:90 to 80:20.

Here, the concentration of polycyclic aromatic hydrocarbons of the diluent oil varies depending on the conditions of the hydrogenation step. However, when the dilution step is carried out under the conditions in which the content (concentration) of polycyclic aromatic hydrocarbons in the hydrogenation product obtainable in the hydrogenation step is 40 mass % or less as described above, the concentration of polycyclic aromatic hydrocarbons in the mixed oil can be adjusted to 5 mass % to 50 mass %, and preferably 15 mass % to 35 mass %, by setting the mass ratio of the heavy fraction and the diluent oil to the range described above.

Furthermore, when the flow rate per unit time of the heavy fraction that is directly supplied from the separation step to the hydrogenation step is constant, the flow rate per unit time of the diluent oil is also made constant and the diluents oil is returned to the hydrogenation step under the conditions in which the mass ratio is in the range described above. Furthermore, when the flow rate per unit time of the heavy fraction varies, the flow rate of the diluent oil is also varied in accordance with this change.

When the mass ratio is adjusted to be in such a range, and the hydrogenation product in the adjusted amount is returned to the hydrogenation step as a diluent oil, heat generation caused by the hydrogenation in the hydrogenation step is suppressed, an extreme increase in the reaction temperature at the hydrogenation reactor is prevented, and an appropriate hydrogenation (for example, conversion from bicyclic aromatic hydrocarbons to naphthenobenzenes) can be achieved. Furthermore, a general hydrogenation reactor can be used. Also, the conversion from polycyclic aromatic hydrocarbons to naphthenobenzenes, which is the main purpose of the hydrogenation step, can be carried out with desired efficiency.

<Hydrogen Recovery Step>

In the hydrogen recovery step, hydrogen is collected from the gas component obtained in the separation step.

Regarding the method of recovering hydrogen, there are no particular limitations as long as hydrogen and other gases that are contained in the gas component obtained in the separation step can be separated, and examples thereof include a pressure swing adsorption method (PSA method), a cryogenic separation method, and a membrane separation method.

<Hydrogen Supply Step>

In the hydrogen supply step, hydrogen obtained in the hydrogen recovery step is supplied to the hydrogenation reactor of the hydrogenation step. The amount of hydrogen supply at that time is regulated depending on the amount of the mixed oil that is supplied to the hydrogenation step. Furthermore, if necessary, the hydrogen pressure is regulated.

When the method includes a hydrogenation supply step as in the present exemplary embodiment, the mixed oil can be hydrogenated using the hydrogen produced as a by-product in the cracking reforming reaction step. A portion or whole of the hydrogen supply from an external source can be reduced by preparing a portion or the entire amount of hydrogen from the by-product hydrogen.

<Recycling Step>

In the recycling step, the other portion of the hydrogenation product of the heavy fraction obtained in the hydrogenation step, that is, the remnant (residual portion) of the hydrogenation product returned to the hydrogenation step in the dilution step, is mixed with the feedstock oil, or is separately returned to the cracking reforming reaction step.

By returning the hydrogenation product of the heavy fraction to the cracking reforming reaction step, the heavy fraction which is a by-product can also be used as a feedstock to obtain monocyclic aromatic hydrocarbons. Therefore, not only the amount of by-products can be reduced, but also the amount of production of monocyclic aromatic hydrocarbons can be increased. Furthermore, since saturated hydrocarbons are also produced by hydrogenation, the hydrogen transfer reaction in the cracking reforming reaction step can be accelerated. From these, the overall yield of monocyclic aromatic hydrocarbons with respect to the amount of supply of the feedstock oil can be enhanced.

Furthermore, when the heavy fraction is directly returned to the cracking reforming reaction step without being hydrogenated treated, since the reactivity of polycyclic aromatic hydrocarbons is low, the yield of monocyclic aromatic hydrocarbons is barely increased.

In this recycling step, the entire amount of the remnant (residual portion) of the hydrogenation product returned to the hydrogenation step in the dilution step may not be necessarily returned to the cracking reforming reaction step. In that case, the hydrogenation product of the heavy fraction that is not returned may be used as a fuel base material or the like.

In regard to the method for producing monocyclic aromatic hydrocarbons of the present exemplary embodiment, since the method includes a hydrogenation step and a recycling step, the heavy fraction which is a by-product can also be used as a feedstock to obtain monocyclic aromatic hydrocarbons. Therefore, not only the amount of by-products can be reduced, but also the amount of production of monocyclic aromatic hydrocarbons can be increased. Accordingly, monocyclic aromatic hydrocarbons having 6 to 8 carbon atoms can be produced with a high yield from a feedstock oil containing polycyclic aromatic hydrocarbons.

Furthermore, since the method includes a dilution step in which a portion of the hydrogenation product of the heavy fraction obtained in the hydrogenation step is returned as a diluent oil to the hydrogenation step, and the concentration of polycyclic aromatic hydrocarbons in the heavy fraction supplied to the hydrogenation step is decreased, extreme heat generation attributable to the hydrogenation of polycyclic aromatic hydrocarbons in the hydrogenation step is suppressed, so that a stabilized hydrogenation is enabled, and a sharp increase in the facility cost of the hydrogenation reactor can be avoided.

Furthermore, in regard to the hydrogenation product of the heavy fraction obtained in the hydrogenation step, a gas component is first separated and removed, and then the heavy fraction obtained in the hydrogenation reaction step can be returned to the cracking reforming reaction step through the recycling step, or can also be supplied to the hydrogenation step as a diluent oil through the dilution step.

Exemplary Embodiment 2

Exemplary Embodiment 2 of the method for producing monocyclic aromatic hydrocarbons related to the first aspect of the invention will be described.

Figure 2:
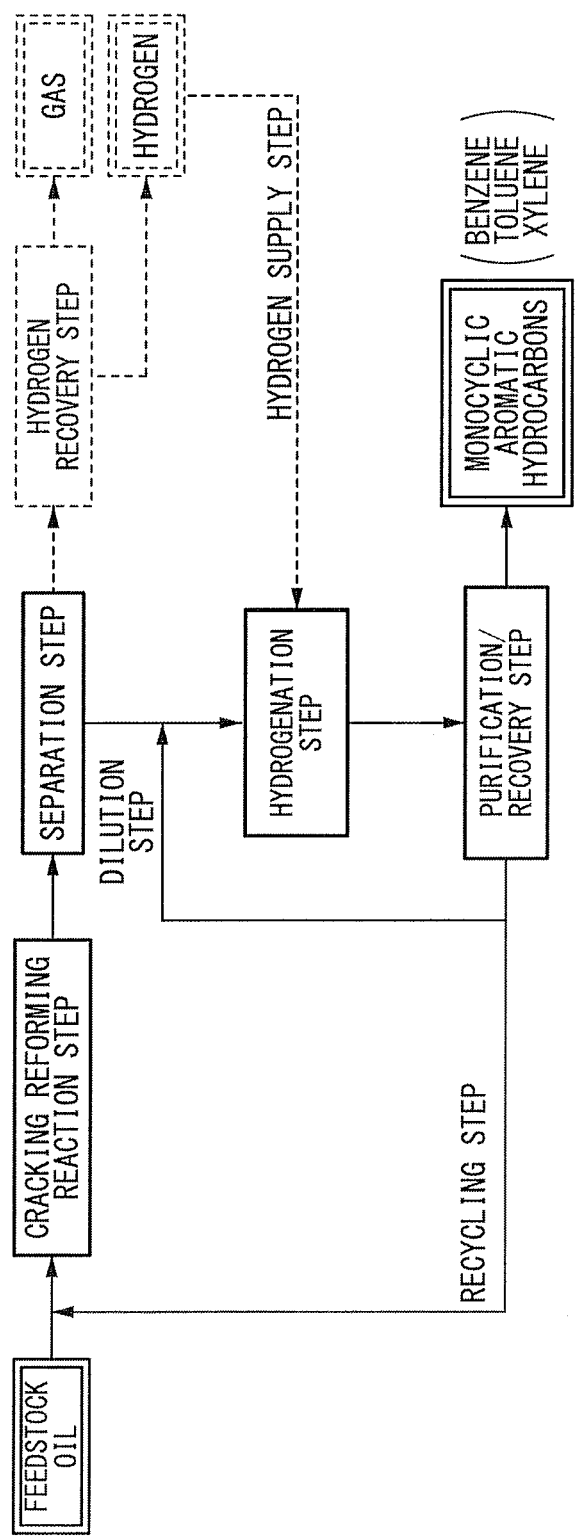
FIG. 2 is a diagram for illustrating Exemplary Embodiment 2 of the method for producing monocyclic aromatic hydrocarbons related to the first aspect of the invention.

FIG. 2 is a diagram for illustrating Exemplary Embodiment 2 of the method for producing monocyclic aromatic hydrocarbons related to the first aspect of the invention, and the method for producing monocyclic aromatic hydrocarbons of the present exemplary embodiment is also a method for producing monocyclic aromatic hydrocarbons having 6 to 8 carbon atoms from feedstock oil.

That is, the method for producing monocyclic aromatic hydrocarbons of the present exemplary embodiment includes, as illustrated in FIG. 2:

(i-1) a cracking reforming reaction step of bringing a feedstock oil into contact with a catalyst for monocyclic aromatic hydrocarbon production to react, and thereby obtaining a product containing monocyclic aromatic hydrocarbons having 6 to 8 carbon atoms and a heavy fraction having 9 or more carbon atoms;

(j-1) a separation step of separating the product produced in the cracking reforming reaction step into a gas component and a liquid component;

(k-1) a hydrogenation step of hydrogenating the liquid component separated in the separation step;

(l-1) a purification/recovery step of distilling the hydrogenation product obtained in the hydrogenation step, and purifying and recovering monocyclic aromatic hydrocarbons;

(m-1) a dilution step of returning a portion of the hydrogenation product of the heavy fraction separated in the purification/recovery step to the hydrogenation step;

(n-1) a recycling step of returning the residual portion of the hydrogenation product of the heavy fraction separated in the purification/recovery step to the cracking reforming reaction step;

(o-1) a hydrogen recovery step of recovering hydrogen that has been produced as a by-product in the cracking reforming reaction step, from the gas component separated in the separation step; and (p-1) a hydrogen supply step of supplying the hydrogen collected in the hydrogen recovery step to the hydrogenation step.

Among the steps (i-1) to (p-1), the steps (i-1), (k-1), (l-1), (m-1) and (n-1) are essential steps for Exemplary Embodiment 2 of the first aspect of the invention, and steps (j-1), (o-1) and (p-1) are optional steps.

The (i-1) cracking reforming reaction step can be carried out in the same manner as in the (a-1) cracking reforming reaction step according to Exemplary Embodiment 1.

The (o-1) hydrogen recovery step can be carried out in the same manner as in the (g-1) hydrogen recovery step according to Exemplary Embodiment 1.

The (p-1) hydrogen supply step can be carried out in the same manner as in the (h-1) hydrogen supply step according to Exemplary Embodiment 1.

In the (j-1) separation step according to the present exemplary embodiment, for example, a form of separating the product into a gas component containing components having 4 or fewer carbon atoms (for example, hydrogen, methane, ethane, and LPG) and a liquid fraction, is employed. In regard to the liquid fraction, since separation is carried out in the (l-1) purification/recovery step, a fraction containing monocyclic aromatic hydrocarbons, a heavy fraction and the like are not separated herein, unlike Exemplary Embodiment 1. However, removing a very heavy fraction that is not suitable for the recycling intended in the present application, or the catalyst powder or the like that is incorporated when a fluidized bed is employed in the cracking reforming reaction step, is appropriately allowed. Even in that case, monocyclic aromatic hydrocarbons, and the heavy fraction intended for hydrogenation and recycling are not separated.

In the (k-1) hydrogenation step according to the present exemplary embodiment, the same hydrogenation catalyst as that used in the (d-1) hydrogenation step according to Exemplary Embodiment 1 can be used.

Furthermore, in the (k-1) hydrogenation step, unlike the (d-1) hydrogenation step according to Exemplary Embodiment 1, since all the liquid component obtained in the separation step is passed through the hydrogenation reactor, the monocyclic aromatic hydrocarbons thus obtained are also hydrogenated. However, hydrogenation of monocyclic aromatic hydrocarbons contradicts the purpose of the invention. Therefore, in the (k-1) hydrogenation step, the amount of loss of the monocyclic aromatic hydrocarbons due to hydrogenation is preferably adjusted to 5 mass % or less when the amount of monocyclic aromatic hydrocarbons before the hydrogenation step is designated as 100 mass %. The reaction conditions to obtain the amount of loss are generally in the range of the reaction conditions according to Exemplary Embodiment 1; however, in order to avoid excessive hydrogenation of the monocyclic aromatic hydrocarbons, it is preferable to carry out the reaction at a higher temperature as compared with Exemplary Embodiment 1.

For example, the hydrogenation temperature may vary depending on the hydrogenation catalyst used, but usually, the hydrogenation temperature is considered to be in the range of usually 250° C. to 450° C., more preferably 300° C. to 400° C., and even more preferably 320° C. to 380° C.

The hydrogenation pressure is preferably set to from 0.7 MPa to 13 MPa. Particularly, the hydrogenation pressure is more preferably set to from 1 MPa to 10 MPa, and even more preferably from 1 MPa to 7 MPa. If the hydrogenation pressure is set to 13 MPa or less, a hydrogenation reactor having a relatively low durable pressure can be used, and the facility cost can be reduced. Furthermore, since the pressure of hydrogen collected in the hydrogen recovery step is usually 13 MPa or less, the collected hydrogen can be used without increasing the pressure. On the other hand, if the pressure is set to 0.7 MPa or greater, the yield of the hydrogenation can be maintained sufficiently appropriately.

The amount of hydrogen consumption may vary depending on the amount of the diluent oil that is conveyed in the dilution step, but the amount of hydrogen consumption is preferably 2000 scfb (337 $Nm^3/m^3$) or less, more preferably 1500 scfb (253 $Nm^3/m^3$) or less, and even more preferably 1000 scfb (169 $Nm^3/m^3$) or less. On the other hand, the amount of hydrogen consumption is preferably 100 scfb (17 $Nm^3/m^3$) or more in view of the yield of the hydrogenation.

The liquid hourly space velocity (LHSV) is preferably set to from 0.1 $h^{-1}$ to 20 $h^{-1}$, and more preferably from 0.2 $h^{-1}$ to 10 $h^{-1}$. If the LHSV is set to 20 $h^{-1}$ or less, polycyclic aromatic hydrocarbons can be sufficiently hydrogenated at a lower hydrogenation pressure. On the other hand, when the LHSV is set to $0.1^{-1}$ or more, an increase in the scale of the hydrogenation reactor can be avoided.

Furthermore, in the (k-1) hydrogenation step according to the present exemplary embodiment, the oil that is directly supplied to the hydrogenation step is the entire liquid fraction (liquid component) obtained in the separation step (provided that a liquid fraction from which a very heavy fraction that is not suitable for the recycling intended in the present application, or the catalyst powder or the like that is incorporated when a fluidized bed is employed in the cracking reforming reaction step has been appropriately removed, may also be used), and contains a large amount of monocyclic aromatic hydrocarbons. Therefore, as compared with the (d-1) hydrogenation step according to Exemplary Embodiment 1, in the present exemplary embodiment, the concentration (content per unit amount) of polycyclic aromatic hydrocarbons in the oil that is directly supplied to the (k-1) hydrogenation step is lower.

In the (l-1) purification/recovery step, monocyclic aromatic hydrocarbons or benzene/toluene/xylene is collected, and a heavy fraction having 9 or more carbon atoms is also separated. Here, the heavy fraction having 9 or more carbon atoms contains a hydrogenation product of polycyclic aromatic hydrocarbons and polycyclic aromatic hydrocarbons that have not been hydrogenated as main components.

In the (m-1) dilution step, similarly to the (e-1) dilution step according to Exemplary Embodiment 1, a portion of the heavy fraction having 9 or more carbon atoms separated in the purification/recovery step is returned as a diluent oil to the hydrogenation step. Thereby, the concentration of polycyclic aromatic hydrocarbons in the product that is supplied to the hydrogenation step is decreased. However, in the present exemplary embodiment, the concentration (content per unit amount) of polycyclic aromatic hydrocarbons in the oil that is directly supplied to the hydrogenation step as described above is lower as compared with Exemplary Embodiment 1. Usually, the concentration of polycyclic aromatic hydrocarbons in the liquid fraction (product) that is directly supplied from the separation step to the hydrogenation step is about 40 mass % to 75 mass %.

Therefore, in order to adjust the concentration of polycyclic aromatic hydrocarbons in the mixed oil that is actually supplied to the hydrogenation step, to from 5 mass % to 50 mass %, and preferably 15 mass % to 35 mass %, as in Exemplary Embodiment 1, the amount of the diluent oil conveyed can be decreased as compared with Exemplary Embodiment 1. Even in this case, the concentration of polycyclic aromatic hydrocarbons in the liquid fraction (product) that is directly supplied from the separation step to the hydrogenation step and the concentration of polycyclic aromatic hydrocarbons in the diluent oil are measured according to, for example, JPI-5S-49 "Petroleum products—Hydrocarbon type test methods—High performance liquid chromatographic method", or are identified by an FID gas chromatographic method, a two-dimensional gas chromatographic method or the like, and thereby the mixing amount of the diluent oil for diluting to the preferred concentration of polycyclic aromatic hydrocarbons described above is determined.

Usually, in this dilution step, the mass ratio of the product that is separated from the product produced in the cracking reforming reaction step and is supplied to the hydrogenation step and the mixed oil composed of a diluent oil is adjusted in the range of 20:80 to 80:20.

Here, the concentration of polycyclic aromatic hydrocarbons in the diluent oil may vary depending on the conditions of the hydrogenation step; however, for example, when the dilution step is carried out under the conditions such that the content (concentration) of polycyclic aromatic hydrocarbons in the heavy fraction having 9 or more carbon atoms obtained after monocyclic aromatic hydrocarbons have been collected in the purification/recovery step is 40 mass % or less, the concentration of polycyclic aromatic hydrocarbons in the mixed oil can be adjusted to 5 mass % to 50 mass %, and preferably 15 mass % to 35 mass %, by adjusting the mass ratio of the heavy fraction and the diluent oil in the range described above.

In the (n-1) recycling step, similarly to the (f-1) recycling step according to Exemplary Embodiment 1, the other portion of the heavy fraction obtained in the purification/recovery step, that is, the remnant (residual portion) of the hydrogenation product returned to the hydrogenation step in the dilution step, is returned to the cracking reforming reaction step as a mixture with the feedstock oil, or separately therefrom.

Since the method for producing monocyclic aromatic hydrocarbons of the present exemplary embodiment also includes a hydrogenation step and a recycling step, monocyclic aromatic hydrocarbons having 6 to 8 carbon atoms can be produced from a feedstock oil containing polycyclic aromatic hydrocarbons with a high yield.

Furthermore, since the method includes a dilution step in which a portion of the hydrogenation product of the heavy fraction obtained in the hydrogenation step is returned as diluent oil to the hydrogenation step, and the concentration of polycyclic aromatic hydrocarbons in the heavy fraction supplied to the hydrogenation step is decreased, extreme heat generation attributable to the hydrogenation of polycyclic aromatic hydrocarbons in the hydrogenation step can be suppressed, and a sharp increase in the facility cost of the hydrogenation reactor can be avoided.

In addition, in the present recycling step, it is not necessarily essential to return the entire amount of the remnant (residual portion) of the hydrogenation product that has been returned to the hydrogenation step in the dilution step, to the cracking reforming reaction step. In that case, the hydrogenation product of the heavy fraction that has not been returned may be used as a fuel base material or the like.

Other Exemplary Embodiments

This invention is not intended to be limited to the exemplary embodiments described above, and can have various modifications to the extent that the gist of the invention is maintained.

For example, regarding the hydrogen that is used in the hydrogenation step, not the by-product produced in the cracking reforming reaction step, but hydrogen obtained by a known hydrogen preparation method may also be utilized. Furthermore, hydrogen produced as a by-product in another catalytic cracking method may also be utilized.

Furthermore, in Exemplary Embodiment 1 or Exemplary Embodiment 2, a heavy fraction discharge step of taking out a certain amount of a portion of the heavy fraction having 9 or more carbon atoms obtained from the fraction separated in the separation step, and discharging the portion out of the system, may be provided. Specifically, in Exemplary Embodiment 1, when the heavy fraction is directly supplied from the separation step to the hydrogenation step, a portion of the heavy fraction may be taken out before being mixed with the diluent oil, and discharged out of the system. Furthermore, it is also acceptable to take out a portion of the heavy fraction after the hydrogenation step or after the dilution step, and to discharge the portion out of the system.

Similarly, also in Exemplary Embodiment 2, a portion of the heavy fraction may be extracted after the hydrogenation step and the dilution step, and discharged out of the system.

Second Aspect

Exemplary Embodiment 1

Hereinafter, Exemplary Embodiment 1 of the method for producing monocyclic aromatic hydrocarbons related to the second aspect of the invention will be described.

Figure 3:
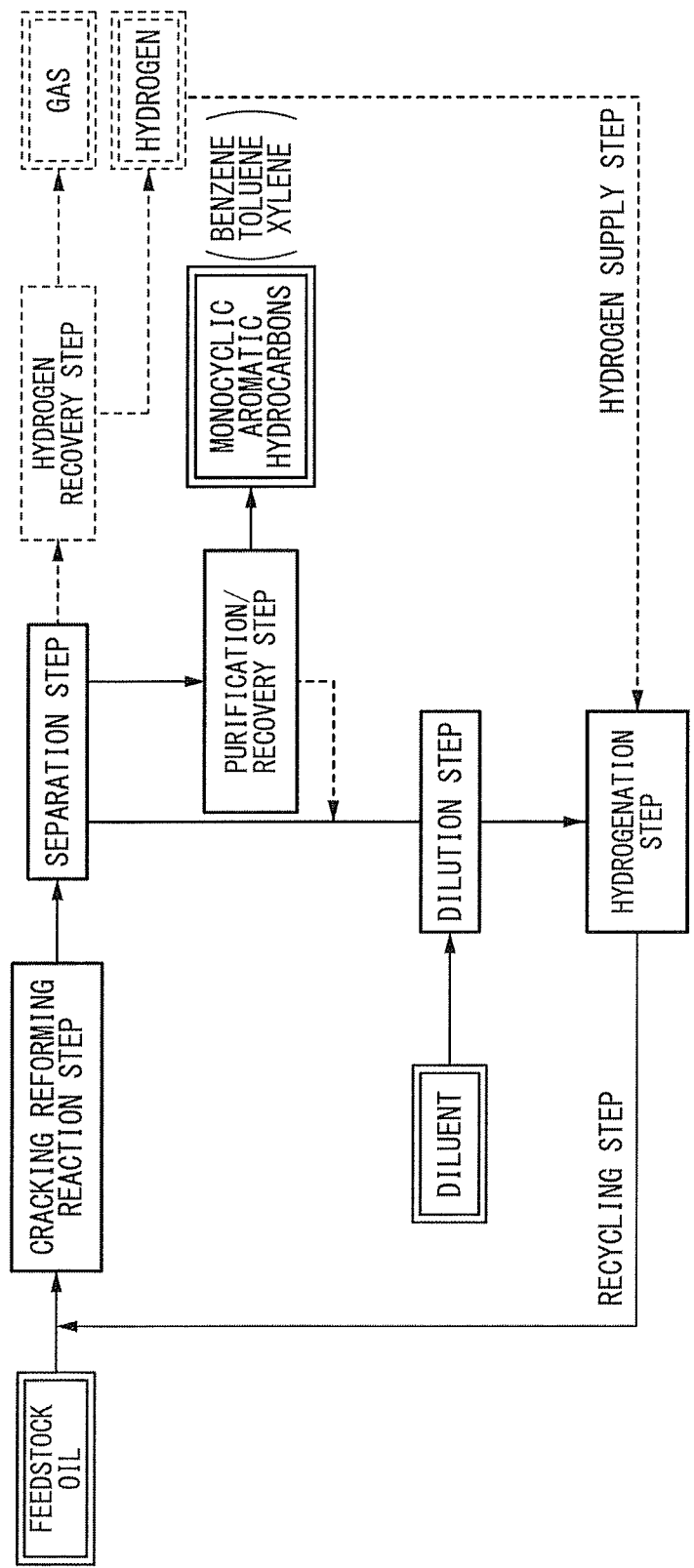
FIG. 3 is a diagram for illustrating Exemplary Embodiment 1 of the method for producing monocyclic aromatic hydrocarbons related to a second aspect of the invention.

FIG. 3 is a diagram for illustrating Exemplary Embodiment 1 of the method for producing monocyclic aromatic hydrocarbons related to the second aspect of the invention, and the method for producing monocyclic aromatic hydrocarbons of the present exemplary embodiment is a method for producing monocyclic aromatic hydrocarbons having 6 to 8 carbon atoms from the feedstock oil.

That is, the method for producing monocyclic aromatic hydrocarbons of the present exemplary embodiment includes, as illustrated in FIG. 3:

(a-2) a cracking reforming reaction step of bringing feedstock oil into contact with a catalyst for monocyclic aromatic hydrocarbon production to react, and thereby obtaining a product containing monocyclic aromatic hydrocarbons having 6 to 8 carbon atoms and a heavy fraction having 9 or more carbon atoms;

(b-2) a separation step of separating the product produced in the cracking reforming reaction step into plural fractions;

(c-2) a purification/recovery step of purifying and recovering the monocyclic aromatic hydrocarbons separated in the separation step;

(d-2) a dilution step of adding a diluent to the heavy fraction having 9 or more carbon atoms separated from the product produced in the cracking reforming reaction step;

(e-2) a hydrogenation step of hydrogenating the mixture obtained in the dilution step;

(f-2) a recycling step of returning the hydrogenation product of the mixture obtained in the hydrogenation step to the cracking reforming reaction step;

(g-2) a hydrogen recovery step of recovering the hydrogen produced as a by-product in the cracking reforming reaction step, from the gas component separated in the separation step; and (h-2) a hydrogen supply step of supplying the hydrogen collected in the hydrogen recovery step to the hydrogenation step.

Among the steps (a-2) to (h-2), steps (a-2), (c-2), (d-2), (e-2), and (f-2) are essential steps in Exemplary Embodiment 1 of the second aspect of the invention, and steps (b-2), (g-2) and (h-2) are optional steps.

Hereinafter, the respective steps will be described in detail.

<Cracking Reforming Reaction Step>

The (a-2) cracking reforming reaction step can be carried out in the same manner as in the (a-1) cracking reforming reaction step according to Exemplary Embodiment 1 of the first aspect.

<Separation Step>

The (b-2) separation step can be carried out in the same manner as in the (b-1) separation step according to Exemplary Embodiment 1 of the first aspect.

<Purification/Recovery Step>

The (c-2) purification/recovery step can be carried out in the same manner as in the (c-1) purification/recovery step according to Exemplary Embodiment 1 of the first aspect.

<Dilution Step>

In the dilution step, a diluent formed of hydrocarbons that has been prepared separately in advance is added to the heavy fraction having 9 or more carbon atoms separated from the product produced in the cracking reforming reaction step, and thereby, the concentration of polycyclic aromatic hydrocarbons in a mixture composed of the heavy fraction having 9 or more carbon atoms and the diluent is made lower than the concentration of polycyclic aromatic hydrocarbons in the heavy fraction. That is, the concentration of polycyclic aromatic hydrocarbons in the heavy fraction supplied to the hydrogenation step that will be described below is decreased to an appropriate concentration.

The heavy fraction that is separated in the separation step and is directly supplied to the hydrogenation step that will be described below (heavy fraction obtainable by excluding the diluent from the mixture) has a very high concentration of the polycyclic aromatic hydrocarbons, for example, as high as 50 mass % to 95 mass %, as described above.

Here, since the polycyclic aromatic hydrocarbons, for example, bicyclic aromatic hydrocarbons occupying a majority thereof, have a large amount of heat generation at the time of the hydrogenation as described above, in the case of a feedstock having a high content ratio of polycyclic aromatic hydrocarbons, in order to carry out the reaction in a stable manner, it is preferable to employ a technique for suppressing an excessive increase in the reaction temperature. In this invention, regarding the method for suppressing the reaction temperature, a general technique can be employed, and techniques such as hydrogen quenching can be used. However, the heavy fraction that is separated in the separation step and is directly supplied to this hydrogenation step, has a very high concentration of polycyclic aromatic hydrocarbons, for example, as high as 50 mass % to 95 mass %, as described above. Therefore, if it is attempted to suppress heat generation only by hydrogen quenching, the configuration of the apparatus for suppressing heat generation becomes very complicated, as compared with a conventional kerosene-gas oil desulfurization apparatus or the like.

Thus, in the present exemplary embodiment, the concentration of polycyclic aromatic hydrocarbons in the oil (mixture) that is supplied to the hydrogenation step is adjusted in advance by means of the dilution step, and the heat generation occurring as a result of the hydrogenation of polycyclic aromatic hydrocarbons is suppressed. Thus, it is possible to cause an appropriate hydrogenation to be carried out sufficiently even with a conventional general hydrogenation reactor.

Regarding the diluent, hydrocarbons that are not easily hydrogenated as compared with polycyclic aromatic hydrocarbons in the hydrogenation step that will be described below, specifically, monocyclic aromatic hydrocarbons such as trimethylbenzene and tetramethylbenzene (including various isomers); cyclohexanes; naphthenes such as decalins; and hydrocarbons including paraffin and the like, are suitably used. At that time, it is necessary to select a feedstock which is compatible with the diluent and the heavy fraction, and if the concentration of the polycyclic aromatic hydrocarbons is very high, it is preferable to select a monocyclic aromatic hydrocarbon or the like. On the other hand, when the hydrogenation conditions are set to a high pressure of, for example, 7 MPa or higher, the monocyclic aromatic hydrocarbon, which is a diluent, may be hydrogenated per se. As such, it is necessary to select an appropriate solvent in accordance with the actual hydrogenation conditions. Furthermore, in the case where the diluent is collected and recycled as the diluent, there is no problem because monocyclic aromatic hydrocarbons also become saturated hydrocarbons and can be utilized as a diluent, and it is also acceptable to use the diluent directly in the cracking reforming reaction step. However, since there is a possibility that a sufficient heat generation preventing effect may not be obtained in the hydrogenation step, care should be taken. Furthermore, regarding the diluent, if the concentration (content) of polycyclic aromatic hydrocarbons is lower than that in the heavy fraction, the diluent may contain the polycyclic aromatic hydrocarbons; however, at that time, the effect of suppressing heat generation is smaller as compared with a diluent which does not contain polycyclic aromatic hydrocarbons. Specifically, base materials for oil refinery which contain the monocyclic aromatic hydrocarbons, naphthenes, paraffins and the like, as well as polycyclic aromatic hydrocarbons, for example, various cracking base materials and straight-run base materials, such as the light cycle oil (LCO) that is also used as the feedstock oil, can also be used.

Furthermore, the concentration of polycyclic aromatic hydrocarbons in such a diluent may be any concentration capable of lowering the concentration of polycyclic aromatic hydrocarbons in the mixture to be formed to an appropriate concentration, and the concentration is considered to be preferably 50 mass % or less, more preferably 30 mass % or less, and even more preferably 20 mass % or less.

Such a diluent is stored in, for example, a storage tank prepared separately, and is supplied therefrom to the line which transports the heavy fraction and mixed with the heavy fraction. Thereby, the diluent lowers the concentration of polycyclic aromatic hydrocarbons in the mixture thus obtainable, to an appropriate concentration.

For example, in this dilution step, it is preferable to form a mixture by adding a diluent to the heavy fraction such that the concentration of polycyclic aromatic hydrocarbons in the mixture composed of the heavy fraction having 9 or more carbon atoms that has been separated from the product produced in the cracking reforming reaction step, and the diluent, that is, a mixture that is actually supplied to the hydrogenation step, is from 5 mass % to 50 mass %. Furthermore, it is more preferable to add the diluent such that the concentration of polycyclic aromatic hydrocarbons is from 15 mass % to 35 mass %.

By adjusting the concentration of polycyclic aromatic hydrocarbons in the mixture to 50 mass % or less, heat generation by the hydrogenation in the hydrogenation step that will be described below is suppressed, an extreme increase in the reaction temperature in the hydrogenation reactor is prevented, and an appropriate hydrogenation (for example, conversion from bicyclic aromatic hydrocarbons to naphthenobenzenes) can be achieved. Furthermore, a general hydrogenation reactor can be used. Furthermore, by adjusting the concentration to 5 mass % or more, the conversion from polycyclic aromatic hydrocarbons to naphthenobenzenes, which is the main purpose of the hydrogenation step, can be carried out with desired efficiency.

However, if the concentration of polycyclic aromatic hydrocarbons in the mixture is too low, the conversion efficiency from polycyclic aromatic hydrocarbons to naphthenobenzenes is not a sufficiently profitable efficiency in terms of cost, and for example, there is a need to increase the size of the hydrogenation reactor. Therefore, in order to further increase the conversion efficiency, it is more preferable to adjust the concentration to 15 mass % or more as described above. Furthermore, in order to suppress heat generation by the hydrogenation more sufficiently, it is more preferable to adjust the concentration to 35 mass % or less.

Furthermore, in this dilution step, the amount of the diluent to be supplied is appropriately determined in order to adjust the concentration of polycyclic aromatic hydrocarbons in the mixture to a concentration such as described above. In that case, the amount of the diluent is largely affected by the concentration of polycyclic aromatic hydrocarbons in the heavy fraction having 9 or more carbon atoms that has been separated from the product produced in the cracking reforming reaction step. That is, if the concentration of polycyclic aromatic hydrocarbons in the heavy fraction is high, the amount of the diluent needs to be increased to a relatively large amount, and if the concentration of polycyclic aromatic hydrocarbons in the heavy fraction is low, the amount of the diluent can be relatively decreased. Furthermore, the amount of the diluent is also largely affected by the concentration of polycyclic aromatic hydrocarbons in the diluent. That is, if the concentration of polycyclic aromatic hydrocarbons in the diluent is high, the amount of the diluent needs to be increased to a relatively large amount, and if the concentration of polycyclic aromatic hydrocarbons in the diluent is low, the amount of the diluent can be relatively decreased.

Usually, the concentration of polycyclic aromatic hydrocarbons in the heavy fraction separated from the product in the separation step as described above is 50 mass % to 95 mass %.

Therefore, in regard to the dilution of the heavy fraction, the concentration of polycyclic aromatic hydrocarbons in the heavy fraction (product) and the concentration of polycyclic aromatic hydrocarbons in the diluent are measured according to, for example, JPI-5S-49 "Petroleum products—Hydrocarbon type test methods—High performance liquid chromatographic method", or are identified by an FID gas chromatographic method, a two-dimensional gas chromatographic method or the like, and the mixing ratio of the heavy fraction and the diluent is determined such that the concentration of polycyclic aromatic hydrocarbons in the mixture obtained after being diluted with the diluent is 5 mass % to 50 mass %, and preferably 15 mass % to 35 mass %, as described above. Usually, if the concentration of polycyclic aromatic hydrocarbons in the diluent is, for example, 20 mass % or less, the mass ratio (mixing ratio) of the heavy fraction separated in the separation step (heavy fraction having 9 or more carbon atoms that is separated in the product produced in the cracking reforming reaction step and is supplied to the hydrogenation step) and the diluent is adjusted to be in the range of 10:90 to 80:20.

Furthermore, when the flow rate per unit time of the heavy fraction that is supplied from the separation step to the hydrogenation step is constant, the flow rate per unit time of the diluent is also made constant under the conditions in which the mass ratio is in the range described above, and the diluent is then added to the heavy fraction. Furthermore, when the flow rate per unit time of the heavy fraction varies, the flow rate of the diluent is also varied in accordance with this variation.

<Hydrogenation Step>

In the hydrogenation step, the mixture formed by adding the diluent to the heavy fraction having 9 or more carbon atoms in the dilution step is hydrogenated. Specifically, the mixture and hydrogen are supplied to a hydrogenation reactor, and at least a portion of polycyclic aromatic hydrocarbons contained in the mixture is hydrogenated using a hydrogenation catalyst. Here, the heavy fraction that is separated in the separation step or the purification/recovery step and is supplied to the hydrogenation step, that is, the heavy fraction having 9 or more carbon atoms, contains a large amount of bicyclic aromatic hydrocarbons (polycyclic aromatic hydrocarbons) such as naphthalene. Furthermore, although the amount is smaller than the heavy fraction, the diluent also contains bicyclic aromatic (polycyclic aromatic) hydrocarbons depending on the type.

Thus, in the hydrogenation step, it is preferable to hydrogenate these polycyclic aromatic hydrocarbons until the hydrocarbons have one aromatic ring each. For example, it is preferable to hydrogenate naphthalene until it becomes tetraline (naphthenobenzene), and also for alkylnaphthalenes such as methylnaphthalene and dimethylnaphthalene, it is preferable to convert them to naphthenobenzene, that is, aromatic hydrocarbons each having one aromatic ring with a tetraline skeleton. Similarly, indenes are preferably converted to aromatic hydrocarbons having an indane skeleton, anthracenes are preferably converted to aromatic hydrocarbons having an octahydroanthracene skeleton, and phenanthrenes are preferably converted to aromatic hydrocarbons having an octahydrophenanthrene skeleton.

If hydrogenation is carried out until the components have one aromatic ring each, when this hydrogenation product is returned to the cracking reforming reaction step in the recycling step that will be described below, the hydrogenation product, particularly aromatic hydrocarbons having a tetraline skeleton, are easily converted to monocyclic aromatic hydrocarbons. As such, in order to increase the yield of monocyclic aromatic hydrocarbons in the cracking reforming reaction step, the content of polycyclic aromatic hydrocarbons in the hydrogenation product obtainable in this hydrogenation step is preferably set to 40 mass % or less, more preferably to 25 mass % or less, and even more preferably to 15 mass % or less.

Furthermore, the content of polycyclic aromatic hydrocarbons in the hydrogenation product thus obtainable is preferably smaller than the content of polycyclic aromatic hydrocarbons in the feedstock oil. In regard to the content of polycyclic aromatic hydrocarbons in the hydrogenation product, that is, the concentration of polycyclic aromatic hydrocarbons, the concentration can be lowered by increasing the amount of the hydrogenation catalyst or increasing the reaction pressure. However, it is not necessary to carry out the hydrogenation treatment until all of the polycyclic aromatic hydrocarbons become saturated hydrocarbons. Excessive hydrogenation brings about an increase in the amount of hydrogen consumption, and also brings about an excessive increase in the amount of heat generation.

Regarding the reaction type in the hydrogenation step, a fixed bed is suitably employed.

Regarding the hydrogenation catalyst, known hydrogenation catalysts (for example, nickel catalysts, palladium catalysts, nickel-molybdenum-based catalysts, cobalt-molybdenum-based catalysts, nickel-cobalt-molybdenum-based catalysts, and nickel-tungsten-based catalysts) can be used.

The hydrogenation temperature may vary depending on the hydrogenation catalyst used, but the hydrogenation temperature is considered to be in the range of usually 100° C. to 450° C., more preferably 200° C. to 400° C., and even more preferably 250° C. to 380° C.

The hydrogenation pressure is preferably set to from 0.7 MPa to 13 MPa. Particularly, the hydrogenation pressure is more preferably set to 1 MPa to 10 MPa, and even more preferably from 1 M Pa to 7 MPa. If the hydrogenation pressure is set to 13 MPa or less, a hydrogenation reactor having a relatively low durable pressure can be used, and the facility cost can be reduced. Furthermore, since the pressure of hydrogen collected in the hydrogen recovering step is usually 13 MPa or less, the hydrogen thus collected can be used without increasing the pressure. On the other hand, if the pressure is set to 0.7 MPa or higher, the yield of the hydrogenation can be maintained sufficiently appropriately.

The amount of hydrogen consumption may vary depending on the amount of the diluent oil that is conveyed in the dilution step that will be described below, but the amount of hydrogen consumption is preferably 2000 scfb (337 Nm$^3$/m$^3$) or less, more preferably 1500 scfb (253 Nm$^3$/m$^3$) or less, and even more preferably 1000 scfb (169 Nm$^3$/m$^3$) or less.

On the other hand, the amount of hydrogen consumption is preferably 100 scfb (17 Nm$^3$/m$^3$) or more from the viewpoint of the yield of the hydrogenation.

The liquid hourly space velocity (LHSV) is preferably set to from 0.1 h$^{-1}$ to 20 h$^{-1}$, and more preferably from 0.2 h$^{-1}$ to 10 h$^{-1}$. If the LHSV is adjusted to 20 h$^{-1}$ or less, polycyclic aromatic hydrocarbons can be sufficiently hydrogenated at a lower hydrogenation pressure. On the other hand, if the liquid hourly space velocity is adjusted to 0.1$^{-1}$ or more, an increase in the size of the hydrogenation reactor can be avoided.

Here, since polycyclic aromatic hydrocarbons, for example, bicyclic aromatic hydrocarbons occupying a majority thereof, have a large amount of heat generation at the time of the hydrogenation as described above, in the case of a feedstock having a high content ratio of polycyclic aromatic hydrocarbons, in order to carry out the reaction in a stable manner, it is preferable to employ a technique for suppressing an excessive increase in the reaction temperature. In this invention, regarding the method for suppressing the reaction temperature, a general technique can be employed, and techniques such as circulating hydrogen gas quenching that is employed in conventional kerosene-gas oil desulfurization apparatuses can be used. However, the heavy fraction separated in the separation step has a very high concentration of polycyclic aromatic hydrocarbons, for example, as high as 50 mass % to 95 mass % as described above. Therefore, if it is attempted to suppress heat generation only by hydrogen quenching, quenching facilities in a number close to a two-digit number are needed, and the configuration around the reaction apparatus for suppressing heat generation becomes very complicated. Furthermore, since the reaction apparatus becomes a reaction apparatus associated with an extremely large amount of heat generation, it is evaluated to be an apparatus with a high risk at the time of emergency operation. However, in the present exemplary embodiment, since a mixture is formed by adding a diluent to the heavy fraction as described above, and the concentration of polycyclic aromatic hydrocarbons in the mixture is set to 5 mass % to 50 mass %, and preferably 15 mass % to 35 mass %, heat generation occurring as a result of the hydrogenation of polycyclic aromatic hydrocarbons is suppressed, and a sufficiently appropriate hydrogenation can be carried out even with a conventional general hydrogenation reactor.

<Hydrogen Recovery Step>

The (g-2) hydrogen recovery step can be carried out in the same manner as in the (g-1) hydrogen recovery step according to Exemplary Embodiment 1 of the first aspect.

<Hydrogen Supply Step>

The (h-2) hydrogen supply step can be carried out in the same manner as in the (h-1) hydrogen recovery step according to Exemplary Embodiment 1 of the first aspect.

<Recycling Step>

In the recycling step, the hydrogenation product of the mixture obtained in the hydrogenation step is mixed with the feedstock oil and is returned to the cracking reforming reaction step.

By returning the hydrogenation product of the mixture to the cracking reforming reaction step, the heavy fraction as a by-product is also used as a feedstock, and thereby monocyclic aromatic hydrocarbons can be obtained. Therefore, not only the amount of by-products can be reduced, but also the amount of production of monocyclic aromatic hydrocarbons can be increased. Furthermore, since saturated hydrocarbons are also produced by hydrogenation, a hydrogen transfer reaction in the cracking reforming reaction step can be accelerated. From these, the overall yield of monocyclic aromatic hydrocarbons relative to the amount of supply of the feedstock can be enhanced.

Furthermore, in the recycling step, the hydrogenation product may not be necessarily entirely recycled to the feedstock oil of the cracking reforming reaction step. In that case, the hydrogenation product that has not been recycled can also be used as a fuel base material.

Furthermore, the monocyclic aromatic hydrocarbons, naphthenes and paraffins in the diluent also contribute to the production of monocyclic aromatic hydrocarbons in the cracking reforming reaction step. Therefore, this diluent also contributes to an increase in the yield of monocyclic aromatic hydrocarbons.

When the heavy fraction is directly returned to the cracking reforming reaction step without being hydrogenation treated, since the polycyclic aromatic hydrocarbons have low reactivity, the yield of monocyclic aromatic hydrocarbons barely increases.

Since the method for producing aromatic hydrocarbons of the present exemplary embodiment includes a hydrogenation step and a recycling step, monocyclic aromatic hydrocarbons can be obtained by using a heavy fraction which is a by-product as a feedstock. Therefore, not only the amount of by-products can be reduced, but also the amount of production of monocyclic aromatic hydrocarbons can be increased. Therefore, monocyclic aromatic hydrocarbons having 6 to 8 carbon atoms can be produced with a high yield from a feedstock oil containing polycyclic aromatic hydrocarbons.

Furthermore, since the method includes a dilution step in which the concentration of polycyclic aromatic hydrocarbons in the mixture obtainable is lowered than the concentration of polycyclic aromatic hydrocarbons in the heavy fraction by adding a diluent to a heavy fraction having 9 or more carbon atoms separated from the product produced in the cracking reforming reaction step, extreme heat generation attributable to the hydrogenation of polycyclic aromatic hydrocarbons in the hydrogenation step is suppressed, a stabilized hydrogenation is enabled, and a sharp increase in the facility cost of the hydrogenation reactor can be avoided.

Exemplary Embodiment 2

Exemplary Embodiment 2 of the method for producing monocyclic aromatic hydrocarbons related to the second aspect of the invention will be described.

Figure 4:
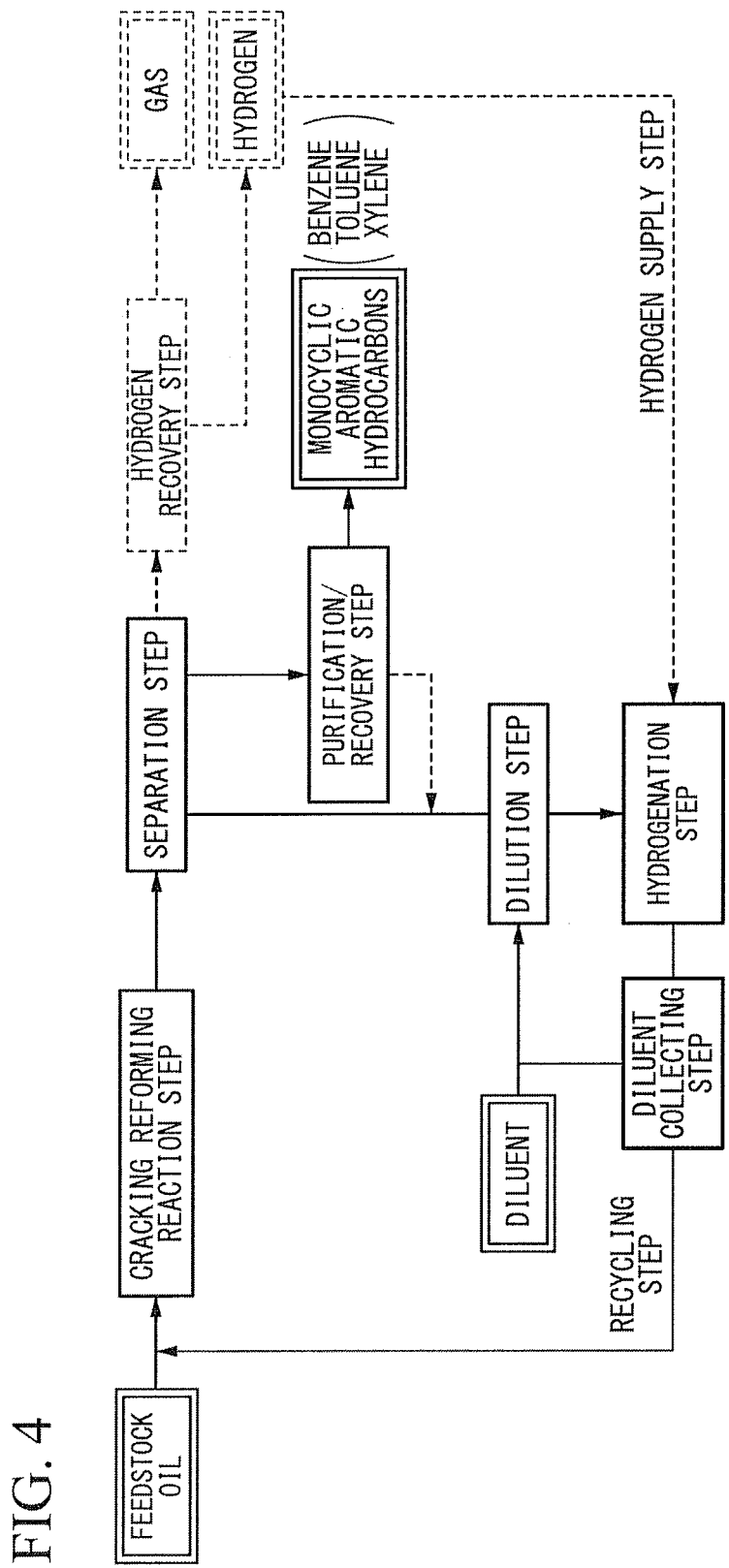
FIG. 4 is a diagram for illustrating Exemplary Embodiment 2 of the method for producing monocyclic aromatic hydrocarbons related to the second aspect of the invention.

FIG. 4 is a diagram for explaining Exemplary Embodiment 2 of the method for producing monocyclic aromatic hydrocarbons related to the second aspect of the invention, and the method or producing monocyclic aromatic hydrocarbons of the present exemplary embodiment is a method for producing monocyclic aromatic hydrocarbons having 6 to 8 carbon atoms from feedstock oil.

That is, the method for producing monocyclic aromatic hydrocarbons of the present exemplary embodiment includes, as illustrated in FIG. 4:

(i-2) a cracking reforming reaction step of bringing feedstock oil into contact with a catalyst for monocyclic aromatic hydrocarbon production to react, and thereby obtaining a product containing monocyclic aromatic hydrocarbons having 6 to 8 carbon atoms, and a heavy fraction having 9 or more carbon atoms;

(j-2) a separation step of separating the product produced in the cracking reforming reaction step into plural fractions;

(k-2) a purification/recovery step of purifying and recovering monocyclic aromatic hydrocarbons separated in the separation step;

(l-2) a dilution step of adding a diluent to a heavy fraction having 9 or more carbon atoms separated from the product produced in the cracking reforming reaction step;

(m-2) a hydrogenation step of hydrogenating the mixture obtained in the dilution step;

(n-2) a diluent recovering step of separating and removing the diluent from the hydrogenation product of the mixture obtained in the hydrogenation step, and recovering the diluent to recycle the diluent as a diluent for the dilution step;

(o-2) a recycling step of returning the hydrogenation product of the mixture obtained in the hydrogenation step to the cracking reforming reaction step;

(p-2) a hydrogen recovery step of recovering hydrogen that is produced as a by-product in the cracking reforming reaction step from the gas component separated in the separation step; and (q-2) a hydrogen supply step of supplying the hydrogen collected in the hydrogen recovery step to the hydrogenation step.

Among the steps (i-2) to (q-2), steps (i-2), (k-2), (l-2), (m-2), (n-2), and (o-2) are essential steps in Exemplary Embodiment 2 of the second aspect of the invention, and steps (j-2), (p-2) and (q-2) are optional steps.

The (i-2) cracking reforming reaction step can be carried out in the same manner as in the (a-2) cracking reforming reaction step according to Exemplary Embodiment 1.

The (j-2) separation step can be carried out in the same manner as in the (b-2) separation step according to Exemplary Embodiment 1.

The (k-2) purification/recovery step can be carried out in the same manner as in the (c-2) purification/recovery step according to Exemplary Embodiment 1.

The (m-2) hydrogenation step can be carried out in the same manner as in the (e-2) hydrogenation step according to Exemplary Embodiment 1.

The (p-2) hydrogen recovery step can be carried out in the same manner as in the (g-2) hydrogen recovery step according to Exemplary Embodiment 1.

The (q-2) hydrogen supply step can be carried out in the same manner as in the (h-2) hydrogen supply step according to Exemplary Embodiment 1.

The (l-2) dilution step according to the present exemplary embodiment is carried out in the same manner as in the (d-2) dilution step according to Exemplary Embodiment 1, and a diluent formed of hydrocarbons is added to the heavy fraction having 9 or more carbon atoms separated in the separation step so as to lower the concentration of polycyclic aromatic hydrocarbons in the mixture composed of the heavy fraction having 9 or more carbon atoms and the diluent to be lower than the concentration of polycyclic aromatic hydrocarbons in the heavy fraction.

Regarding the diluent used in the present exemplary embodiment, instead of using hydrocarbons stored in a storage tank that is separately prepared as in Exemplary Embodiment 1, a diluent collected in the diluent recovering step that will be described below is used by recycling. However, in the case where the diluent is not fully collected at the time of start-up or in the diluent recovering step, and there is a lack of diluent, hydrocarbons are supplied from a storage tank or the like that is separately prepared.

Therefore, regarding the diluent, unlike Exemplary Embodiment 1, a diluent that can be easily separated and collected from the hydrogenation product in the diluent recovering step, specifically, a diluent that is easily separated from hydrogenation products of polycyclic aromatic hydrocarbons (particularly naphthenobenzenes) by a distillation operation, is used. Furthermore, as this diluent, hydrocarbons that are not easily hydrogenated are used as in the case of Exemplary Embodiment 1. Accordingly, polycyclic aromatic hydrocarbons and the like which have a higher boiling point than naphthenobenzenes and are prone to undergo a hydrogenation, are not mainly included thereto. Since the diluent of the present exemplary embodiment is circulated any number of times through the hydrogenation step, the diluent recovering step, and the dilution step as illustrated in FIG. 4, there may be occurrences in which some of the diluent may not be collected in the recovery step or the like so that the amount of the diluent is reduced, or in which the heavy fraction is partially cracked or the like so as to be collected as the diluent in the diluent recovering step, so that the amount of the diluent increases. Therefore, if necessary, there is a need to control the amount of circulation of the diluent. However, in any case, a material which is not easily subjected to hydrogenation and cracking more than necessary in the hydrogenation step is preferred.

Therefore, regarding such hydrocarbons, for example, hydrocarbons that can be produced in the hydrogenation step and have a boiling point lower than that of t-decalin (t-decahydronaphthalene) having a boiling point of 185° C. are suitably used. That is, naphthenes, paraffins, or monocyclic aromatic compounds, which can be easily separated from polycyclic aromatic hydrocarbons or naphthenobenzenes by a distillation operation and are not easily hydrogenated, are suitably used as diluents.

In addition, the dilution step of the present exemplary embodiment is the same as the dilution step of Exemplary Embodiment 1, except that such a diluent is used. That is, in regard to the concentration of polycyclic aromatic hydrocarbons of the mixture formed by diluting with a diluent, the dilution step is the same as the dilution step of Exemplary Embodiment 1. Furthermore, regarding the rate of dilution, that is, the mass ratio (mixing ratio) of the heavy fraction and the diluent, may vary depending on the diluent; since a diluent which does not basically include polycyclic aromatic hydrocarbons in the present exemplary embodiment is used, the amount of addition of the diluent can be reduced compared to the mass ratio according to Exemplary Embodiment 1.

<Diluent Recovering Step>

In the diluent recovering step, the diluent is separated and removed from the hydrogenation product of the mixture obtained in the hydrogenation step, and the diluent is collected. Then, the diluent thus collected is recycled as a diluent to be added to the heavy fraction having 9 or more carbon atoms in the dilution step.

Regarding the method of separating and removing the diluent from the hydrogenation product of the mixture, a distillation operation is suitably employed as described above. That is, in this diluent recovering step, for example, components having a boiling point lower than 185° C. and components having a boiling point higher than this are separated by means of a distillation column. Thereby, for example, components having a boiling point lower than 185° C. can be separated from components having a boiling point higher than 185° C. Therefore, the separated components having a boiling point lower than 185° C., that is, diluent components are cooled to condensate, and thereby a diluent can be regenerated.

Therefore, this is sent to the dilution step and added to the heavy fraction to form a mixture, and thereafter, this mixture is circulated through the hydrogenation step, the diluent recovering step, and the dilution step in sequence.

In the (o-2) recycling step, unlike Exemplary Embodiment 1, instead of returning the entire amount of the hydrogenation product of the mixture obtained in the hydrogenation step directly to the cracking reforming reaction step, the fraction from which the diluent has been separated in the diluent recovering step is mixed with the feedstock oil, or is returned to the cracking reforming reaction step separately.

Even in the method for producing monocyclic aromatic hydrocarbons of the present exemplary embodiment, since the hydrogenation step and the recycling step are included, monocyclic aromatic hydrocarbons having 6 to 8 carbon atoms can be produced with a high yield from a feedstock oil containing polycyclic aromatic hydrocarbons.

Furthermore, since the method includes a dilution step, extreme heat generation of polycyclic aromatic hydrocarbons in the hydrogenation step is suppressed, and a sharp increase in the facility cost of the hydrogenation reactor can be avoided.

Moreover, since the method includes a diluent recovering step of separating and removing the diluent from the hydrogenation product of the mixture, and recovering and recycling the diluent, as the diluent is circulated, a step of continuously supplying a fresh diluent is unnecessary. Thus, the operation conditions can be simplified.

Other Exemplary Embodiments

The present invention is not intended to be limited to the exemplary embodiments, and various modifications can be made to the extent that the gist of the invention is maintained.

For example, regarding the hydrogen to be used in the hydrogenation step, not the hydrogen produced as a by-product in the cracking reforming reaction step, but hydrogen that is obtained by a known hydrogen production method may be utilized. Furthermore, hydrogen produced as a by-product by another catalytic cracking method may also be utilized. Furthermore, it is also acceptable to send monocyclic aromatic hydrocarbons altogether to the hydrogenation step to be separated thereafter. In that case, the recovery step for the monocyclic aromatic hydrocarbons having 6 to 8 carbon atoms and the diluent recovering step may also be combined.

Also, in the exemplary embodiments described above, a heavy fraction discharge step in which a portion of the heavy fraction having 9 or more carbon atoms obtained from the fraction separated in the separation step is extracted in a certain amount and is discharged out of the system, may also be provided. Specifically, when the heavy fraction is directly supplied from the separation step to the hydrogenation step, a portion of the heavy fraction may be extracted and discharged out of the system before the heavy fraction is mixed with a diluent in the dilution step.

Furthermore, in the exemplary embodiments described above, the purification/recovery step is carried out after the separation step, but the invention is not limited to this. For example, the separation step may be carried out after the hydrogenation step.

EXAMPLES

Hereinafter, the present invention will be described more specifically based on Examples and Comparative Examples, but the invention is not intended to be limited to these Examples.

[Preparation Example for Catalyst for Monocyclic Aromatic Hydrocarbon Production]

Preparation of Catalyst Containing Gallium and Phosphorus-Supported Crystalline Aluminosilicate:

A solution (A) formed from 1706.1 g of sodium silicate (J Sodium Silicate No. 3, $SiO_2$: 28 mass % to 30 mass %, Na: 9 mass % to 10 mass %, balance: water, manufactured by Nippon Chemical industrial Co., Ltd.) and 2227.5 g of water, and a solution (B) formed from 64.2 g of $Al_2(SO_4)_3 \cdot 14\text{-}18H_2O$ (special grade reagent, manufactured by Wako Pure Chemical Industries, Ltd.), 369.2 g of tetrapropylammonium bromide, 152.1 g of $H_2SO_4$ (97 mass %), 326.6 g of NaCl, and 2975.7 g of water, were respectively prepared.

Next, while the solution (A) was stirred at room temperature, the solution (B) was slowly added to the solution (A).

The mixture thus obtained was vigorously stirred for 15 minutes, and the gel was crushed to an emulsion-like homogenous and fine state.

Next, this mixture was introduced into an autoclave made of stainless steel, and under the conditions of a temperature of 165° C., a time of 72 hours, and a stirring rate of 100 rpm, a crystallization operation was carried out under the self-pressure. After completion of the crystallization operation, the product was filtered, and a solid product was collected. The solid product was subjected to washing using about 5 liters of deionized water and filtration repeatedly for 5 times. The solid obtained by separation by filtration was dried at 120° C., and under an air stream, the solid was calcined at 550° C. for 3 hours.

The calcination product thus obtained was subjected to an X-ray diffraction analysis (model name: RIGAKU RINT-2500V), and as a result, it was confirmed that the calcination product had an MFI structure. Furthermore, the $SiO_2/Al_2O_3$ ratio (molar ratio) obtained by a fluorescent X-ray analysis (model name: RIGAKU ZSX101e) was 64.8. Furthermore, the aluminum element contained in the lattice structure as calculated from these results was 1.32 mass %.

Next, a 30 mass % aqueous solution of ammonium nitrate was added to the calcination product thus obtained at a proportion of 5 mL per gram of the calcination product, and the mixture was heated and stirred for 2 hours at 100° C., and then subjected to filtration and washing with water. These operations were repeated 4 times, and then the product was dried for 3 hours at 120° C. Thus, an ammonium type crystalline aluminosilicate was obtained.

Thereafter, calcination was carried out for 3 hours at 780° C., and a proton type crystalline aluminosilicate was obtained.

Subsequently, 120 g of the proton type crystalline aluminosilicate thus obtained was impregnated with 120 g of an aqueous solution of gallium nitrate so that 0.4 mass % (value based on 100 mass % of the total mass of the crystalline aluminosilicate) of gallium would be supported, and the resultant was dried at 120° C. Thereafter, under an air stream, the resultant was calcinated for 3 hours at 780° C., and a gallium-supported crystalline aluminosilicate was obtained.

Next, 30 g of the gallium-supported crystalline aluminosilicate thus obtained was impregnated with 30 g of an aqueous solution of diammonium hydrogen phosphate such that 0.7 mass % of phosphorus (value based on 100 mass % of the total mass of the crystalline aluminosilicate) would be supported, and the resultant was dried at 120° C. Thereafter, under an air stream, the resultant was calcinated for 3 hours at 780° C., and a catalyst A containing crystalline aluminosilicate, gallium and phosphorus was obtained.

In the following Examples 1A to 5A, the heavy fraction separated from the product obtained in the cracking reforming reaction step based on Exemplary Embodiment 1 according to the first aspect of the invention as illustrated in FIG. 1, was hydrogenated in the hydrogenation step, and a portion of the heavy fraction hydrogenation product was returned to the hydrogenation step as a diluent oil. In the dilution step, regarding the heavy fraction hydrogenation product for diluting the heavy fraction in the dilution step, oils that have been hydrogenated under the same hydrogenation conditions as those used in the hydrogenation step in the respective Examples were used.

First Aspect

Example 1A

LCO (10 vol % distillation temperature: 215° C., 90 vol % distillation temperature: 318° C.) indicated in Table 1, which was feedstock oil, was brought into contact with the catalyst A (MFI type zeolite having 0.4 mass % of gallium and 0.7 mass % of phosphorus supported thereon) in a fluidized bed reactor under the conditions of reaction temperature: 538° C., reaction pressure: 0.3 MPaG; and a contact time for contact between the LCO and the zeolite component contained in the catalyst of 12 seconds, and was allowed to react. Thus, a cracking reforming reaction step was carried out. Subsequently, the content of polycyclic aromatic hydrocarbons in the heavy fraction obtained after recovering monocyclic aromatic hydrocarbons having 6 to 8 carbon atoms was measured using a two-dimensional gas chromatography apparatus (manufactured by ZOEX Corp., KT2006 GC×GC system), and the content was 87 mass %.

Next, the heavy fraction was hydrogenated using a commercially available nickel-molybdenum catalyst under the conditions of a reaction temperature of 350° C., a reaction pressure of 3 MPa, and a LHSV of 0.5 h$^{-1}$. A portion of the heavy fraction hydrogenation product thus obtained was returned as diluent oil to the hydrogenation step, such that the mass ratio of the heavy fraction and the diluent oil was 40/60. At this time, the content of polycyclic aromatic hydrocarbons in the mixed oil of the heavy fraction and the diluent oil was 50 mass %. The general conditions for the dilution step and the hydrogenation step are described in Table 2. For the hydrogen used in the hydrogenation step, the hydrogen separated in the hydrogen recovery step was used.

Furthermore, the heavy fraction hydrogenation product obtained by treating the mixed oil of the heavy fraction and the diluent oil in the hydrogenation step was recycled to the cracking reforming reaction step, and thus production of monocyclic aromatic hydrocarbons having 6 to 8 carbon atoms was carried out under the cracking reforming reaction step conditions. The amount of the monocyclic aromatic hydrocarbons having 6 to 8 carbon atoms thus obtained was 46 mass %.

TABLE 1

| | Feedstock properties | | | Analysis method |
|---|---|---|---|---|
| Density at 15° C. | | g/cm³ | 0.9258 | JIS K 2249 |
| Dynamic viscosity at 30° C. | | mm²/s | 2.817 | JIS K 2283 |
| Distillation properties | Initial distillation point | ° C. | 173 | JIS K 2254 |
| | 10 vol % distillation temperature | ° C. | 215 | |
| | 50 vol % distillation temperature | ° C. | 266 | |
| | 90 vol % distillation temperature | ° C. | 318 | |
| | End point | ° C. | 346 | |
| Composition analysis | Saturated fraction | vol % | 22.9 | JPI-5S-49 |
| | Olefin fraction | vol % | 2.1 | |
| | Whole aromatic fraction | vol % | 75 | |
| | Monocyclic aromatic fraction | vol % | 27.6 | |
| | Bicyclic aromatic fraction | vol % | 39.5 | |
| | Tricyclic or higher-cyclic aromatic fraction | vol % | 7.9 | |

Example 2A

Production of monocyclic aromatic hydrocarbons having 6 to 8 carbon atoms was carried out in the same manner as in Example 1A, except that in the dilution step, the diluent oil was returned to the hydrogenation step such that the mass ratio of the heavy fraction and the diluent oil would be 33/67 (the content of polycyclic aromatic hydrocarbons in the mixed oil of the heavy fraction and the diluent oil was 44 mass %). The amount of monocyclic aromatic hydrocarbons having 6 to 8 carbon atoms thus obtained was 45 mass %.

Example 3A

Production of monocyclic aromatic hydrocarbons having 6 to 8 carbon atoms was carried out in the same manner as in Example 1A, except that in the dilution step, the diluent oil was returned to the hydrogenation step such that the mass ratio of the heavy fraction and the diluent oil would be 17/83 (the content of polycyclic aromatic hydrocarbons in the mixed oil of the heavy fraction and the diluent oil was 34 mass %). The amount of monocyclic aromatic hydrocarbons having 6 to 8 carbon atoms thus obtained was 44 mass %.

Example 4A

Production of monocyclic aromatic hydrocarbons having 6 to 8 carbon atoms was carried out in the same manner as in Example 1A, except that the reaction pressure in the hydrogenation step was set to 5 MPa, and in the dilution step, the diluent oil was returned to the hydrogenation step such that the mass ratio of the heavy fraction and the diluent oil would be 17/83 (the content of polycyclic aromatic hydrocarbons in the mixed oil of the heavy fraction and the diluent oil was 22 mass %). The amount of monocyclic aromatic hydrocarbons having 6 to 8 carbon atoms thus obtained was 41 mass %.

Example 5A

Production of monocyclic aromatic hydrocarbons having 6 to 8 carbon atoms was carried out in the same manner as in Example 1A, except that the reaction pressure in the hydrogenation step was set to 5 MPa, and in the dilution step, the diluent oil was returned to the hydrogenation step such that the mass ratio of the heavy fraction and the diluent oil would be 5/95 (the content of polycyclic aromatic hydrocarbons in the mixed oil of the heavy fraction and the diluent oil was 13 mass %). The amount of monocyclic aromatic hydrocarbons having 6 to 8 carbon atoms thus obtained was 42 mass %.

Comparative Example 1A

Production of monocyclic aromatic hydrocarbons having 6 to 8 carbon atoms was carried out in the same manner as in Example 1A, except that dilution of the heavy fraction was not carried out. The amount of monocyclic aromatic hydrocarbons having 6 to 8 carbon atoms thus obtained was 46 mass %.

The following results are shown in Table 2.

"Heavy fraction/heavy fraction hydrogenation product": Mass ratio of the heavy fraction and the diluent oil "Polycyclic aromatics after dilution": Concentration (mass %) of polycyclic aromatic hydrocarbons in the mixed oil (mixed oil of the heavy fraction and the diluent oil) after being diluted in the dilution step "Reaction pressure": Reaction pressure (MPa) in the hydrogenation step "Polycyclic aromatics after hydrogenation": Concentration (mass %) of polycyclic aromatic hydrocarbons in the hydrogenation product after the hydrogenation step "Heavy fraction processing rate per unit time": Processing rate of the heavy fraction per unit time (undiluted Comparative Example 1 was taken as 100)

"Amount of heat generation": Calculated value of the amount of heat generation per kg of the oil supplied to the hydrogenation step (undiluted Comparative Example 1 was taken as 100)

"Monocyclic aromatics having 6 to 8 carbon atoms": Amount (mass %) of monocyclic aromatic hydrocarbons having 6 to 8 carbon atoms obtained in the cracking reforming reaction step that when diluent oil was added to the heavy fraction, the concentration of polycyclic aromatic hydrocarbons was decreased, and heat generation was relatively suppressed. Thereby, operation of the hydrogenation can be carried out in a stable manner even in adiabatic large-sized reactors and the like.

Example 6A

First, based on Exemplary Embodiment 2 related to the first aspect of the invention as illustrated in FIG. 2, LCO (10 vol % distillation temperature: 215° C., 90 vol % distillation temperature: 318° C.) indicated in Table 1, which was feedstock oil, was brought into contact with the catalyst A (MFI type zeolite having 0.4 mass % of gallium and 0.7 mass % of phosphorus supported thereon) in a fluidized bed reactor under the conditions of reaction temperature: 538° C., reaction pressure: 0.3 MPaG, and a contact time for contact between the LCO and the zeolite component contained in the catalyst of 12 seconds, and was allowed to react. Thus, a cracking reforming reaction step was carried out. A gas component was separated from the product obtained in the cracking reforming reaction step, and the liquid component was collected and analyzed using a two-dimensional gas chromatography apparatus (manufactured by ZOEX Corp., KT2006 GC×GC system), and it was confirmed that 48 mass % of monocyclic aromatic hydrocarbons were included.

Thereafter, the collected liquid component was hydrogenated using a commercially available nickel-molybdenum catalyst under the conditions of a reaction temperature of 350° C., a reaction pressure of 3 MPaG, and a LHSV of 0.5 $h^{-1}$.

Next, monocyclic aromatic hydrocarbons having 6 to 8 carbon atoms were collected from the hydrogenation product of the liquid component by distillation, and a portion of the heavy fraction hydrogenation product having 9 or more car-

TABLE 2

| | | Example 1A | Example 2A | Example 3A | Example 4A | Example 5A | Comparative Example 1A |
|---|---|---|---|---|---|---|---|
| Dilution step | Heavy fraction/Heavy fraction hydrogenation product (mass ratio) | 40/60 | 33/67 | 17/83 | 17/83 | 5/95 | Undiluted |
| | Polycyclic aromatics after dilution, mass % | 50 | 44 | 34 | 22 | 13 | 87 |
| Hydrogenation Reaction step | Reaction pressure, MPa | 3 | 3 | 3 | 5 | 5 | 3 |
| | Polycyclic aromatics after hydrogenation, mass % | 21 | 20 | 19 | 11 | 9 | 22 |
| | Heavy fraction processing rate per unit time (value calculated relative to Comparative Example 1A as 100) | 50 | 33 | 17 | 17 | 5 | 100 |
| | Amount of heat generation (value calculated relative to Comparative Example 1A as 100) | 49 | 40 | 20 | 35 | 7 | 100 |
| Cracking reforming Reaction step | Monocyclic aromatics having 6 to 8 carbon atoms, mass % | 46 | 45 | 44 | 41 | 42 | 46 |

From the results shown in Table 2, as compared with Comparative Example 1A in which the heavy fraction was directly hydrogenated without diluting (undiluted), it was confirmed that in Examples 1A to 5A that were diluted, the calculated value of the amount of heat generation per kg of the oil supplied to the hydrogenation step decreased. This implies bon atoms was returned as diluent oil to the hydrogenation step such that the mass ratio of the liquid component after the separation step and the diluent oil would be 50/50 (the content of polycyclic aromatic hydrocarbons in the mixed oil of the liquid component after the separation step and the diluent oil was 32 mass %).

Subsequently, the mixed oil containing the liquid component after the separation step and the diluent oil was hydrogenated under the hydrogenation conditions. Regarding the hydrogen used in the hydrogenation step, the hydrogen separated in the hydrogen recovery step was used.

Thereafter, monocyclic aromatic hydrocarbons having 6 to 8 carbon atoms were collected by distillation from the hydrogenation product of the mixed oil of the liquid component after the separation step and the diluent oil, and the heavy fraction hydrogenation product having 9 or more carbon atoms was recycled to the cracking reforming reaction step. Thus, production of monocyclic aromatic hydrocarbons having 6 to 8 carbon atoms was carried out under the cracking reforming reaction step conditions. The amount of monocyclic aromatic hydrocarbons having 6 to 8 carbon atoms thus obtained was 46 mass %.

Example 7A

Production of monocyclic aromatic hydrocarbons having 6 to 8 carbon atoms was carried out in the same manner as in Example 6A, except that in the dilution step, the diluent oil was returned to the hydrogenation step such that the mass ratio of the liquid component after the separation step and the diluent oil would be 33/67 (the content of polycyclic aromatic hydrocarbons in the mixed oil of the liquid component after the separation step and the diluent oil was 29 mass %). The amount of monocyclic aromatic hydrocarbons having 6 to 8 carbon atoms thus obtained was 45 mass %.

Comparative Example 2A

Production of monocyclic aromatic hydrocarbons having 6 to 8 carbon atoms was carried out in the same manner as in Example 6A, except that dilution of the heavy fraction was not carried out. The amount of monocyclic aromatic hydrocarbons having 6 to 8 carbon atoms was 44 mass %.

The following results are shown in Table 3.

"Liquid component after separation step/heavy fraction hydrogenation product": Mass ratio of the liquid component after the separation step and diluent oil "Polycyclic aromatics after dilution": Concentration (mass %) of polycyclic aromatic hydrocarbons in the mixed oil (mixed oil of the liquid component after the separation step and the diluent oil) after being diluted in the dilution step "Reaction pressure": Reaction pressure (MPa) in the hydrogenation step "Polycyclic aromatics after hydrogenation": Concentration (mass %) of polycyclic aromatic hydrocarbons in the hydrogenation product after the hydrogenation step "Heavy fraction processing rate per unit time": Processing rate of the heavy fraction per unit time (undiluted Comparative Example 2 was taken as 100)

"Amount of heat generation": Calculated value of the amount of heat generation per kg of the oil supplied to the hydrogenation step (undiluted Comparative Example 2 was taken as 100)

"Monocyclic aromatics having 6 to 8 carbon atoms": Amount (mass %) of monocyclic aromatic hydrocarbons having 6 to 8 carbon atoms obtained in the cracking reforming reaction step

TABLE 3

| | | Example 6A | Example 7A | Comparative Example 2A |
|---|---|---|---|---|
| Dilution step | Liquid component after separation step/Heavy fraction hydrogenation product (mass ratio) | 50/50 | 33/67 | Undiluted |
| | Polycyclic aromatics after dilution, mass % | 32 | 29 | 42 |
| Hydrogenation reaction step | Reaction pressure, MPa | 3 | 3 | 3 |
| | Polycyclic aromatics after hydrogenation, mass % | 17 | 19 | 11 |
| | Heavy fraction processing rate per unit time (value calculated relative to Comparative Example 2A as 100) | 50 | 33 | 100 |
| | Amount of heat generation (value calculated relative to Comparative Example 2A as 100) | 63 | 42 | 100 |
| Cracking reforming Reaction step | Monocyclic aromatics having 6 to 8 carbon atoms, mass % | 46 | 45 | 44 |

From the results shown in Table 3, as compared with Comparative Example 2A in which the liquid component after the separation step was directly hydrogenated without diluting (undiluted), it was confirmed that in Examples 6A and 7A that were diluted, the calculated value of the amount of heat generation per kg of the oil supplied to the hydrogenation step decreased. This implies that when diluent oil was added to the heavy fraction, the concentration of polycyclic aromatic hydrocarbons was decreased, and heat generation was relatively suppressed. Thereby, operation of the hydrogenation can be carried out in a stable manner even in adiabatic large-sized reactors and the like.

Second Aspect

A diluent was added to the heavy fraction separated from the product obtained in the cracking reforming reaction step to dilute the heavy fraction, in the following Examples 1B to 3B based on Exemplary Embodiment 1 related to the second aspect of the invention shown in FIG. 4, and in Examples 4B to 7B based on Exemplary Embodiment 2 related to the second aspect of the invention shown in FIG. 5.

Example 1B

LCO (10 vol % distillation temperature: 215° C., 90 vol % distillation temperature: 318° C.) indicated in Table 1, which was feedstock oil, was brought into contact with the catalyst A (MFI type zeolite having 0.4 mass % of gallium and 0.7 mass % of phosphorus supported thereon) in a fluidized bed reactor under the conditions of reaction temperature: 538° C., reaction pressure: 0.3 MPaG, and a contact time for contact between the LCO and the zeolite component contained in the catalyst of 12 seconds, and was allowed to react. Thus, a cracking reforming reaction step was carried out. Subsequently, monocyclic aromatic hydrocarbons having 6 to 8 carbon atoms thus obtained were collected by distillation. The content of polycyclic aromatic hydrocarbons in the heavy fraction having 9 or more carbon atoms obtained after removing the monocyclic aromatic hydrocarbons having 6 to 8 carbon atoms was measured using a two-dimensional gas chromatography apparatus (manufactured by ZOEX Corp., KT2006 GC×GC system), and the content was 87 mass %.

Next, 1,3,5-trimethylbenzene (TMB) was added as a diluent to the heavy fraction such that the mass ratio would be 17/83 (heavy fraction/diluent). Thereafter, the mixed oil of the heavy fraction and the diluent (the content of polycyclic aromatic hydrocarbons was 15 mass %) was hydrogenated using a commercially available nickel-molybdenum catalyst under the conditions of a reaction temperature of 350° C., a reaction pressure of 5 MPa, and a LHSV of 0.5 h$^{-1}$. Regarding the hydrogen used in the hydrogenation step, the hydrogen separated in the hydrogen recovery step was used.

Furthermore, the hydrogenation product obtained by treating the mixed oil of the heavy fraction and the diluent in the hydrogenation step, was recycled to the cracking reforming reaction step, and production of monocyclic aromatic hydrocarbons having 6 to 8 carbon atoms was carried out under the cracking reforming reaction step conditions. The amount of monocyclic aromatic hydrocarbons having 6 to 8 carbon atoms was 62 mass %.

Example 2B

Production of monocyclic aromatic hydrocarbons having 6 to 8 carbon atoms was carried out in the same manner as in Example 1B, except that in the dilution step, gas oil having the properties indicated in Table 4 was used as the diluent. The content of polycyclic aromatic hydrocarbons in the mixed oil of the heavy fraction and the diluent was 18 mass %. The amount of monocyclic aromatic hydrocarbons having 6 to 8 carbon atoms thus obtained was 45 mass %.

Example 3B

Production of monocyclic aromatic hydrocarbons having 6 to 8 carbon atoms was carried out in the same manner as in Example 1B, except that in the dilution step, a mixture of 50 mass % of 1,3,5-trimethylbenzene (TMB) and 50 mass % of normal decane was used as the diluent. The content of polycyclic aromatic hydrocarbons in the mixed oil of the heavy fraction and the diluent was 15 mass %. The amount of monocyclic aromatic hydrocarbons having 6 to 8 carbon atoms thus obtained was 53 mass %.

Example 4B

LCO (10 vol % distillation temperature: 215° C., 90 vol % distillation temperature: 318° C.) indicated in Table 1, which was feedstock oil, was brought into contact with the catalyst A (MFI type zeolite having 0.4 mass % of gallium and 0.7 mass % of phosphorus supported thereon) in a fluidized bed reactor under the conditions of reaction temperature: 538° C., reaction pressure: 0.3 MPaG, and a contact time for contact between the LCO and the zeolite component contained in the catalyst of 12 seconds, and was allowed to react. Thus, a cracking reforming reaction step was carried out. Subsequently, monocyclic aromatic hydrocarbons having 6 to 8 carbon atoms thus obtained were collected by distillation. The content of polycyclic aromatic hydrocarbons in the heavy fraction having 9 or more carbon atoms obtained after removing the monocyclic aromatic hydrocarbons having 6 to 8 carbon atoms was measured using a two-dimensional gas chromatography apparatus (manufactured by ZOEX Corp., KT2006 GC×GC system), and the content was 87 mass %.

Next, 1,3,5-trimethylbenzene (TMB) was added as a diluent to the heavy fraction such that the mass ratio would be 5/95 (heavy fraction/diluent) (dilution step). Thereafter, the mixed oil of the heavy fraction and the diluent (the content of polycyclic aromatic hydrocarbons was 8 mass %) was hydrogenated using a commercially available nickel-molybdenum catalyst under the conditions of a reaction temperature of 350° C., a reaction pressure of 5 MPa, and a LHSV of 0.5 h$^{-1}$. Regarding the hydrogen used in the hydrogenation step, the hydrogen separated in the hydrogen recovery step was used.

Furthermore, the hydrogenation product obtained by treating the mixed oil of the heavy fraction and the diluent in the hydrogenation step, was fractionated into a fraction having a boiling point higher than 185° C. and a fraction having a boiling point of 185° C. or lower, and the fraction having a boiling point lower than 185° C. was returned to a point before the hydrogenation step to be reused as a diluent. The

TABLE 4

| | Properties of gas oil for dilution | | | Analysis method |
|---|---|---|---|---|
| Density at 15° C. | | g/cm³ | 0.8549 | JIS K 2249 |
| Dynamic viscosity at 30° C. | | mm²/s | 2.716 | JIS K 2283 |
| Sulfur fraction | | mass ppm | 27 | JIS K 2541 |
| Distillation properties | Initial boiling point | ° C. | 179 | JIS K 2254 |
| | 10 vol % distillation temperature | ° C. | 203 | |
| | 50 vol % distillation temperature | ° C. | 257 | |
| | 90 vol % distillation temperature | ° C. | 294 | |
| | End point | ° C. | 308 | |
| Composition analysis | Saturated fraction | vol % | 63.4 | JPI-5S-49 |
| | Olefin fraction | vol % | 0.6 | |
| | Whole aromatic fraction | vol % | 36 | |
| | Monocyclic aromatic fraction | vol % | 33.4 | |
| | Bicyclic aromatic fraction | vol % | 2.4 | |
| | Tricyclic or higher-cyclic aromatic fraction | vol % | 0.2 | | fraction having a boiling point of 185° C. or higher was recycled to the cracking reforming reaction step, and production of monocyclic aromatic hydrocarbons having 6 to 8 carbon atoms was carried out under the cracking reforming reaction step conditions. The amount of monocyclic aromatic hydrocarbons having 6 to 8 carbon atoms was 44 mass %.

Example 5B

Production of monocyclic aromatic hydrocarbons having 6 to 8 carbon atoms was carried out in the same manner as in Example 4B, except that in the dilution step, a mixture of 50 mass % of 1,3,5-trimethylbenzene (TMB) and 50 mass % of normal decane was used as the diluent and the mixing ratio of the heavy fraction and the diluent was set to 50/50 as a mass ratio; and in the hydrogenation step, the reaction pressure was set to 3 MPa. The content of polycyclic aromatic hydrocarbons in the mixed oil of the heavy fraction and the diluent was 44 mass %. The amount of monocyclic aromatic hydrocarbons having 6 to 8 carbon atoms thus obtained was 46 mass %.

Example 6B

Production of monocyclic aromatic hydrocarbons having 6 to 8 carbon atoms was carried out in the same manner as in Example 4B, except that in the dilution step, the mixing ratio of the heavy fraction and the diluent was set to 33/67 as a mass ratio. The content of polycyclic aromatic hydrocarbons in the mixed oil of the heavy fraction and the diluent was 32 mass %. The amount of monocyclic aromatic hydrocarbons having 6 to 8 carbon atoms thus obtained was 45 mass %.

Example 7B

Production of monocyclic aromatic hydrocarbons having 6 to 8 carbon atoms was carried out in the same manner as in Example 4B, except that in the dilution step, the mixing ratio of the heavy fraction and the diluent was set to 17/83 as a mass ratio, and the reaction pressure in the hydrogenation step was set to 7 MPa. The content of polycyclic aromatic hydrocarbons in the mixed oil of the heavy fraction and the diluent was 15 mass %. The amount of monocyclic aromatic hydrocarbons having 6 to 8 carbon atoms thus obtained was 43 mass %.

Comparative Example 1B

Production of monocyclic aromatic hydrocarbons having 6 to 8 carbon atoms was carried out in the same manner as in Example 1B, except that dilution of the heavy fraction was not carried out. The amount of monocyclic aromatic hydrocarbons having 6 to 8 carbon atoms thus obtained was 44 mass %.

The following results are shown in Table 5.

"Diluent": Kind of diluent (in the case of a mixture, the respective mass ratios for the components are shown in the lower line)

"Heavy fraction/diluent": Mass ratio of the heavy fraction and the diluent

"Polycyclic aromatics after dilution": Concentration (mass %) of polycyclic aromatic hydrocarbons in the mixture after being diluted in the dilution step "Reaction pressure": Reaction pressure (MPa) in the hydrogenation step "Polycyclic aromatics after hydrogenation": Concentration (mass %) of polycyclic aromatic hydrocarbons in the hydrogenation product after the hydrogenation step "Hydrogenation conversion ratio of diluent": Ratio (%) of the diluent that has been hydrogenated "Heavy fraction processing rate per unit time": Processing rate of the heavy fraction per unit time (undiluted Comparative Example 1 was taken as 100)

"Amount of heat generation": Calculated value of the amount of heat generation per kg of the oil supplied to the hydrogenation step (undiluted Comparative Example 1 was taken as 100)

"Separation of diluent by distillation": Presence or absence of diluent recovering step "Monocyclic aromatics having 6 to 8 carbon atoms": Amount (mass %) of monocyclic aromatic hydrocarbons having 6 to 8 carbon atoms obtained in the cracking reforming reaction step

TABLE 5

| | | Example B | Example 2B | Example 3B | Example 4B | Example 5B | Example 6B | Example 7B | Comparative Example 1B |
|---|---|---|---|---|---|---|---|---|---|
| Dilution step | Diluent (in case of mixture: lower line indicates mass %) | TMB | Gas oil | TMB/decane (50/50) | TMB | TMB/decane (50/50) | TMB | TMB | — |
| | Heavy fraction/diluent (mass ratio) | 17/83 | 17/83 | 17/83 | 5/95 | 50/50 | 33/67 | 17/83 | Undiluted |
| | Polycyclic aromatics after dilution (mass %) | 15 | 18 | 15 | 8 | 44 | 32 | 15 | 87 |
| Hydrogenation step | Reaction pressure (MPa) | 5 | 5 | 5 | 5 | 3 | 5 | 7 | 5 |
| | Polycyclic aromatics after hydrogenation (mass %) | 4 | 5 | 3 | 4 | 11 | 6 | 3 | 13 |
| | Hydrogenation conversion ratio of diluent (%) | 1 | — | 0 | 2 | 0 | 1 | 4 | — |
| | Heavy fraction processing rate per unit time (value calculated relative to Comparative Example 1B as 100) | 17 | 17 | 17 | 5 | 50 | 33 | 17 | 100 |
| | Amount of heat generation (value calculated relative to Comparative Example 1B as 100) | 18 | 17 | 18 | 6 | 50 | 36 | 19 | 100 |
| Cracking reforming reaction step | Separation of diluent by distillation | None | None | None | Done | Done | Done | Done | — |
| | Monocyclic aromatics having 6 to 8 carbon atoms (mass %) | 62 | 45 | 53 | 44 | 46 | 45 | 43 | 44 |

From the results shown in Table 5, as compared with Comparative Example 1B in which the heavy fraction was directly hydrogenated without being diluted (undiluted), it was confirmed that in Examples 1B to 7B that had been diluted, the calculated value of the amount of heat generation per kg of the oil supplied to the hydrogenation step decreased. This implies that when a diluent was added to the heavy fraction, the concentration of polycyclic aromatic hydrocarbons was decreased, and heat generation was relatively suppressed. Thereby, operation of the hydrogenation can be carried out in a stable manner even in adiabatic large-sized reactors and the like. Furthermore, the hydrogenation conversion ratio of the diluent was also very low, and it was found that even in the case of recovering the diluent, the diluent could effectively be used by recycling.

INDUSTRIAL APPLICABILITY

According to the method for producing monocyclic aromatic hydrocarbons of the present invention, monocyclic aromatic hydrocarbons having 6 to 8 carbon atoms can be produced with a high yield from a feedstock oil containing polycyclic aromatic hydrocarbons. Furthermore, since the method includes a dilution step, the extreme heat generation attributable to the hydrogenation of polycyclic aromatic hydrocarbons in the hydrogenation step is suppressed, and a stabilized hydrogenation is enabled. Thus, a sharp increase in the facility cost for the hydrogenation reactor can be avoided. Therefore, the present invention is highly useful from an industrial viewpoint.

The invention claimed is:

1. A method for producing monocyclic aromatic hydrocarbons, by which monocyclic aromatic hydrocarbons having 6 to 8 carbon atoms are produced from a feedstock oil having a 10 vol % distillation temperature of 140° C. or higher and a 90 vol % distillation temperature of 380° C. or lower, the method comprising:
  a cracking reforming reaction step of bringing the feedstock oil into contact with a catalyst for monocyclic aromatic hydrocarbon production comprising a crystalline aluminosilicate to effect a reaction, wherein saturated hydrocarbons contained in the feedstock oil are used as a hydrogen donating source, polycyclic aromatic hydrocarbons are partially hydrogenated by a hydrogen transfer reaction from the saturated hydrocarbons, ring-opening is carried out and the polycyclic aromatic hydrocarbons are converted to monocyclic aromatic hydrocarbons, thereby obtaining a product containing monocyclic aromatic hydrocarbons having 6 to 8 carbon atoms and a heavy fraction having 9 or more carbon atoms;
  a separation step of separating the product produced in the cracking reforming reaction step into a plurality of fractions;
  a purification/recovery step of purifying and recovering monocyclic aromatic hydrocarbons separated in the separation step;
  a hydrogenation step of hydrogenating the heavy fraction having 9 or more carbon atoms separated from the product produced in the cracking reforming reaction step;
  a dilution step of adding a portion of a hydrogenation product of the heavy fraction having 9 or more carbon atoms obtained in the hydrogenation step, or a diluent to the heavy fraction having 9 or more carbon atoms separated from the product produced in the cracking reforming reaction step; and
  a recycling step of returning the other portion of the hydrogenation product of the heavy fraction obtained in the hydrogenation step to the cracking reforming reaction step.

2. The method for producing monocyclic aromatic hydrocarbons according to claim 1, by which monocyclic aromatic hydrocarbons having 6 to 8 carbon atoms are produced from a feedstock oil having a 10 vol % distillation temperature of 140° C. or higher and a 90 vol % distillation temperature of 380° C. or lower, the method further comprising:
  a purification/recovery step of purifying and recovering monocyclic aromatic hydrocarbons having 6 to 8 carbon atoms separated from the product produced in the cracking reforming reaction step;
  a dilution step of returning a portion of a hydrogenation product of the heavy fraction having 9 or more carbon atoms obtained in the hydrogenation step, as a diluent oil to the hydrogenation step.

3. The method for producing monocyclic aromatic hydrocarbons having 6 to 8 carbon atoms according to claim 2, wherein in the dilution step, the amount of the diluent oil returned to the hydrogenation step is adjusted such that the mass ratio of the heavy fraction having 9 or more carbon atoms that is separated from the product produced in the cracking reforming reaction step and is supplied to the hydrogenation step, to the diluent oil is in the range of 10:90 to 80:20.

4. The method for producing monocyclic aromatic hydrocarbons according to claim 1, by which monocyclic aromatic hydrocarbons having 6 to 8 carbon atoms are produced from a feedstock oil having a 10 vol % distillation temperature of 140° C. or higher and a 90 vol % distillation temperature of 380° C. or lower, the method further comprising:
  a hydrogenation step of hydrogenating a portion separated from the product produced in the cracking reforming reaction step;
  a purification/recovery step of distilling the hydrogenation product obtained in the hydrogenation step to purify monocyclic aromatic hydrocarbons having 6 to 8 carbon atoms, recovering the monocyclic aromatic hydrocarbons, and separating a heavy fraction having 9 or more carbon atoms from the monocyclic aromatic hydrocarbons having 6 to 8 carbon atoms;
  a dilution step of returning a portion of the heavy fraction having 9 or more carbon atoms separated in the purification/recovery step, as a diluent oil to the hydrogenation step.

5. The method for producing monocyclic aromatic hydrocarbons having 6 to 8 carbon atoms according to claim 4, wherein in the dilution step, the amount of the diluent oil returned to the hydrogenation step is adjusted such that the mass ratio of the product that is separated from the product produced in the cracking reforming reaction step and is supplied to the hydrogenation step, to the diluent oil is in the range of 20:80 to 80:20.

6. The method for producing monocyclic aromatic hydrocarbons having 6 to 8 carbon atoms according to claim 2, wherein in the dilution step, the diluent oil is returned to the hydrogenation step such that the concentration of polycyclic aromatic hydrocarbons in a mixed oil of the product that is separated from the product produced in the cracking reforming reaction step and is supplied to the hydrogenation step, and the diluent oil is 5 mass % to 50 mass %.

7. The method for producing monocyclic aromatic hydrocarbons having 6 to 8 carbon atoms according to claim 2, wherein in the hydrogenation step, the hydrogenation pressure is set to 0.7 MPa to 13 MPa.

8. The method for producing monocyclic aromatic hydrocarbons according to claim 1, by which monocyclic aromatic hydrocarbons having 6 to 8 carbon atoms are produced from a feedstock oil having a 10 vol % distillation temperature of 140° C. or higher and a 90 vol % distillation temperature of 380° C. or lower, the method further comprising:
- a purification/recovery step of purifying and recovering monocyclic aromatic hydrocarbons having 6 to 8 carbon atoms separated from the product produced in the cracking reforming reaction step;
- a dilution step of adding a diluent comprising hydrocarbons to the heavy fraction having 9 or more carbon atoms separated from the product produced in the cracking reforming reaction step;
- a hydrogenation step of hydrogenating the mixture; and
- a recycling step of returning the hydrogenation product of the mixture obtained in the hydrogenation step to the cracking reforming reaction step.

9. The method for producing monocyclic aromatic hydrocarbons having 6 to 8 carbon atoms according to claim 8, further comprising a diluent recovering step of separating and removing the diluent from the hydrogenation product of the mixture obtained in the hydrogenation step, recovering the diluent, and reutilizing the diluent as a diluent to be added to the heavy fraction having 9 or more carbon atoms.

10. The method for producing monocyclic aromatic hydrocarbons having 6 to 8 carbon atoms according to claim 9, wherein a hydrocarbon oil having a boiling point lower than 185° C. is used as the diluent.

11. The method for producing monocyclic aromatic hydrocarbons having 6 to 8 carbon atoms according to claim 8, wherein a diluent having a concentration of polycyclic aromatic hydrocarbons of 50 mass % or less is used as the diluent.

12. The method for producing monocyclic aromatic hydrocarbons having 6 to 8 carbon atoms according to claim 8, wherein in the dilution step, the amount of the diluent is adjusted such that the mass ratio of the heavy fraction having 9 or more carbon atoms that is separated from the product produced in the cracking reforming reaction step and is supplied to the hydrogenation step, to the diluent is in the range of 10:90 to 80:20.

13. The method for producing monocyclic aromatic hydrocarbons having 6 to 8 carbon atoms according to claim 8, wherein in the dilution step, the diluent is added such that the concentration of polycyclic aromatic hydrocarbons in the mixture obtainable by adding the diluent to the heavy fraction having 9 or more carbon atoms, is 5 mass % to 50 mass %.

14. The method for producing monocyclic aromatic hydrocarbons having 6 to 8 carbon atoms according to claim 8, wherein in the hydrogenation step, the hydrogenation pressure is set to 0.7 MPa to 13 MPa.

15. The method for producing monocyclic aromatic hydrocarbons according to claim 1, wherein the hydrogenation temperature of the hydrogenation step is in a range of 100° C. to 450° C.

16. A method for producing monocyclic aromatic hydrocarbons, by which monocyclic aromatic hydrocarbons having 6 to 8 carbon atoms are produced from a feedstock oil having a 10 vol % distillation temperature of 140° C. or higher and a 90 vol % distillation temperature of 380° C. or lower, the method comprising:
- a cracking reforming reaction step of bringing the feedstock oil into contact with a catalyst for monocyclic aromatic hydrocarbon production comprising a crystalline aluminosilicate to effect a reaction, wherein saturated hydrocarbons contained in the feedstock oil are used as a hydrogen donating source, polycyclic aromatic hydrocarbons are partially hydrogenated by a hydrogen transfer reaction from the saturated hydrocarbons, ring-opening is carried out and the polycyclic aromatic hydrocarbons are converted to monocyclic aromatic hydrocarbons, thereby obtaining a product containing monocyclic aromatic hydrocarbons having 6 to 8 carbon atoms and a heavy fraction having 9 or more carbon atoms;
- a separation step of separating the product produced in the cracking reforming reaction step into a plurality of fractions;
- a purification/recovery step of purifying and recovering monocyclic aromatic hydrocarbons separated in the separation step;
- a hydrogenation step of hydrogenating a liquid fraction separated from the product produced in the cracking reforming reaction step at a hydrogenation temperature of 250° C. to 450° C.;
- a dilution step of adding a portion of a hydrogenation product of the heavy fraction having 9 or more carbon atoms obtained in the hydrogenation step, or a diluent to the liquid fraction; and
- a recycling step of returning the other portion of the hydrogenation product of the heavy fraction obtained in the hydrogenation step to the cracking reforming reaction step.

* * * * *